US008858576B2

(12) United States Patent
Takahashi et al.

(10) Patent No.: US 8,858,576 B2
(45) Date of Patent: Oct. 14, 2014

(54) TISSUE FASTENING TOOL, STENT, APPLICATOR FOR PLACING THE SAME, AND TISSUE FASTENING METHOD THROUGH NATURAL ORIFICE

(75) Inventors: Shinji Takahashi, Tokyo (JP); Masatoshi Sato, Yokohama (JP); Tetsuya Yamamoto, Hannou (JP); Kunihide Kaji, Tokyo (JP); Kensuke Hayashi, Yokohama (JP); Takayuki Suzuki, Yokohama (JP)

(73) Assignee: Olympus Medical Systems Corp., Tokyo (JP)

( * ) Notice: Subject to any disclaimer, the term of this patent is extended or adjusted under 35 U.S.C. 154(b) by 1064 days.

(21) Appl. No.: 11/852,730

(22) Filed: Sep. 10, 2007

(65) Prior Publication Data

US 2009/0069822 A1   Mar. 12, 2009

(51) Int. Cl.
*A61B 17/04* (2006.01)
*A61B 17/11* (2006.01)
*A61B 17/064* (2006.01)
*A61B 17/068* (2006.01)
*A61B 17/00* (2006.01)

(52) U.S. Cl.
CPC ........... *A61B 17/064* (2013.01); *A61B 17/1114* (2013.01); *A61B 2017/00867* (2013.01); *A61B 17/068* (2013.01); *A61B 2017/115* (2013.01)
USPC ............................ 606/151; 606/213; 606/215

(58) Field of Classification Search
None
See application file for complete search history.

(56) References Cited

U.S. PATENT DOCUMENTS

| 5,810,851 | A  | * | 9/1998  | Yoon ............................. 606/148 |
| 5,925,054 | A  |   | 7/1999  | Taylor et al. |
| 5,954,747 | A  |   | 9/1999  | Clark |
| 6,113,611 | A  | * | 9/2000  | Allen et al. .................... 606/151 |
| 6,231,587 | B1 | * | 5/2001  | Makower ....................... 606/198 |
| 6,579,311 | B1 | * | 6/2003  | Makower ...................... 623/1.23 |
| 6,652,541 | B1 | * | 11/2003 | Vargas et al. ................. 606/153 |
| 6,663,633 | B1 | * | 12/2003 | Pierson, III ................... 606/148 |
| 6,685,726 | B2 | * | 2/2004  | Black et al. ................... 606/213 |
| 6,709,442 | B2 | * | 3/2004  | Miller et al. .................. 606/153 |
| 6,790,218 | B2 | * | 9/2004  | Jayaraman .................... 606/191 |
| 6,986,784 | B1 | * | 1/2006  | Weiser et al. .................. 623/1.1 |

(Continued)

FOREIGN PATENT DOCUMENTS

EP        1961388 A2    8/2008
JP    2003-506132 A    2/2003

(Continued)

OTHER PUBLICATIONS

Notice of Reasons for Rejection dated Oct. 16, 2012 from corresponding Japanese Patent Application No. 2008-231210, together with an English language translation.

(Continued)

*Primary Examiner* — Melanie Tyson
*Assistant Examiner* — Todd J Scherbel
(74) *Attorney, Agent, or Firm* — Scully, Scott, Murphy & Presser, P.C.

(57) ABSTRACT

A tissue fastening tool which fastens a first biological tissue and a second biological tissue adjacent to the first biological tissue, includes a first tissue fixing section which is hooked onto the first biological tissue and the second tissue fixing section which is hooked onto a second biological tissue adjacent to the first biological tissue.

15 Claims, 28 Drawing Sheets

(56) References Cited

U.S. PATENT DOCUMENTS

| | | | |
|---|---|---|---|
| 7,101,402 B2 * | 9/2006 | Phelps et al. | 623/23.7 |
| 2002/0111620 A1 | 8/2002 | Cooper et al. | |
| 2004/0044364 A1 | 3/2004 | DeVries et al. | |
| 2004/0073237 A1 * | 4/2004 | Leinsing | 606/151 |
| 2004/0098043 A1 * | 5/2004 | Trout, III | 606/213 |
| 2005/0143763 A1 | 6/2005 | Ortiz et al. | |
| 2005/0187564 A1 * | 8/2005 | Jayaraman | 606/141 |
| 2005/0267495 A1 | 12/2005 | Ginn et al. | |
| 2005/0288685 A1 | 12/2005 | Gulles et al. | |
| 2006/0025790 A1 | 2/2006 | de Winter et al. | |
| 2006/0212047 A1 * | 9/2006 | Abbott et al. | 606/142 |
| 2006/0253143 A1 | 11/2006 | Edoga et al. | |
| 2007/0060858 A1 * | 3/2007 | Sogard et al. | 604/8 |
| 2007/0112383 A1 | 5/2007 | Conlon et al. | |
| 2008/0208161 A1 * | 8/2008 | Kaji et al. | 604/500 |
| 2008/0208214 A1 * | 8/2008 | Sato et al. | 606/139 |
| 2011/0152886 A1 * | 6/2011 | Sato et al. | 606/139 |

FOREIGN PATENT DOCUMENTS

| | | |
|---|---|---|
| JP | 2003-529396 A | 10/2003 |
| JP | 2005-193044 | 7/2005 |
| WO | WO 97/32526 | 9/1997 |
| WO | WO 00/07506 | 2/2000 |
| WO | WO 00/36997 A1 | 6/2000 |
| WO | WO 00/66007 A1 | 11/2000 |
| WO | WO 01/10314 A2 | 2/2001 |
| WO | WO 01/10341 A2 | 2/2001 |
| WO | WO 0202163 A2 | 1/2002 |
| WO | WO 02/19923 | 3/2002 |
| WO | WO 02/19923 A1 | 3/2002 |
| WO | WO 2004/004579 A1 | 1/2004 |
| WO | WO 2007/005996 A2 | 1/2007 |
| WO | WO 2007/024615 A1 | 3/2007 |

OTHER PUBLICATIONS

Extended European Search Report dated Jul. 15, 2011 for European Application No. EP 11 00 3392.5.

Extended European Search Report dated Jul. 13, 2011 for corresponding European Application No. EP 11 00 3389.1.

* cited by examiner

TISSUE FASTENING TOOL, STENT, APPLICATOR FOR PLACING THE SAME, AND TISSUE FASTENING METHOD THROUGH NATURAL ORIFICE

BACKGROUND OF THE INVENTION

1. Field of the Invention

The present invention relates to an applicator and tissue fastening method to perform a procedure for fastening tissues through a natural orifice.

2. Description of Related Art

Transcutaneous insertion of medical instruments as a treatment of body organs is well known. This method is less invasive compared to incising the abdomen, and quick recovery is anticipated. A medical instrument used for transcutaneous procedures has a shaft made of hard material inserted in the body transcutaneously, with forceps and so on provided at the front end of the shaft. For example, a treatment instrument used in applications such as connecting hollow organs is disclosed in Japanese Unexamined Patent Application, First Publication No. 2005-193044. This intraluminal anastomosis device has a grasper that can freely open and close fitted to the front end of the shaft, and a fastening tool inserted in the shaft. The fastening tool can be pushed out from the front end of the shaft by the protruding device located proximally with respect to the operator. The fastening tool is formed by annealing (or heat treating) shape memory alloy into a flat coil shape and inserting it in the shaft in the elongated condition. When the fastening tool is used, the clamp is pushed out from the protruding device and inserted into the body. The fastening tool is heated by body temperature and restored to its original coil shape. The hollow organs are joined by the restored fastening tool.

Other examples of dispensing the fastening tool are disclosed in the international publication number WO2002/019923. Here, the fastening tool is pushed out from the needle and dispensed to the tissue. For this reason, an anchor is provided to control the depth to which the needle pierces the tissue and the length of the fastening tool dispensed into the tissue. When performing the procedure, the instrument containing the fastening tool and the needle is punctured to the tissue. The needle is advanced to pierce the layers of tissue, and the position of the fastening tool is fixed by the anchor. Thereafter, the needle is pulled out from the tissue. The fastening tool does not move because of the anchor; therefore, its front end part remains inside of the inside layer of tissue. When the instrument is removed from the tissue, the rest of the fastening tool remains outside of the outside layer of tissue. When the fastening tool is restored into its original coil shape, the layers of the tissue are fastened.

SUMMARY OF THE INVENTION

The present invention relates to a tissue fastening tool which fastens a first biological tissue and a second biological tissue adjacent to the first biological tissue. The tissue fastening tool includes: a first tissue fixing section which is hooked onto the first biological tissue; and a second tissue fixing section which is hooked onto the second biological tissue.

A stent related to the present invention includes: a dilating portion in which the diameter increases from a front end to substantially a rear end of the dilating portion; an indwelled portion which is disposed behind the dilating portion; and a through hole which passes through the dilating portion and the indwelled portion in the longitudinal direction of the stent. The dilating portion penetrates the biological tissues along with dilating a perforation previously formed in the biological tissues by pushing the dilating portion into the perforation; and the indwelled portion is indwelled within the perforation dilated by the dilating portion after the dilating portion penetrates through the biological tissues.

An applicator related to the present invention includes: a tubular puncturing tool housing a tissue fastening tool; a fastening tool pusher which is inserted into the puncturing tool and dispenses the tissue fastening tool inserted into the puncturing tool from a distal end of the puncturing tool; and a sheath in which the puncturing tool is inserted and shifts the stent attached at the distal end of the sheath relative to the puncturing tool.

A tissue fastening apparatus related to the present invention includes: a tissue fastening tool provided with a first tissue fixing section which is hooked onto a first biological tissue and a second tissue fixing section which is hooked onto a second biological tissue adjacent to the first biological tissue; a stent provided with a dilating portion having a diameter which increases from a front end to a rear end of the dilating portion, an indwelled portion which is connected the dilating portion, and a through hole which passes through the dilating portion and the indwelled portion in a longitudinal direction of the stent; and an applicator provided with a tubular puncturing tool in which the tissue fastening tool is inserted, a fastening tool pusher inserted into the puncturing tool to dispenses the tissue fastening tool inserted into the puncturing tool from a distal end of the puncturing tool, and a sheath into which the puncturing tool is inserted to shift the stent which is detachably disposed at the distal end of the sheath relative to the puncturing tool.

The present invention relates to a tissue fastening method for fastening a first biological tissue and a second biological tissue adjacent to the first biological tissue to coalesce the biological tissues, using a tissue fastening tool which includes a first tissue fixing section hooked onto the first biological tissue and a second tissue fixing section hooked onto the second biological tissue. The tissue fastening method includes the steps of:

dispensing the second tissue fixing section of the tissue fastening tool inserted into the tubular puncturing tool from a distal end of the puncturing tool so as to make the second fixing section penetrate through the first and second biological tissues in sequence; and dispensing the first tissue fixing section of the tissue fastening tool from a distal end of the puncturing tool so as not to make first fixing section penetrate through the first and second biological tissues. The second tissue fixing section which has penetrated through the first and second tissues is hooked onto the second biological tissue, and a first tissue fixing section is hooked onto the first biological tissue.

DETAILED DUODENUM DESCRIPTION OF THE INVENTION

First Embodiment

Figure 1:
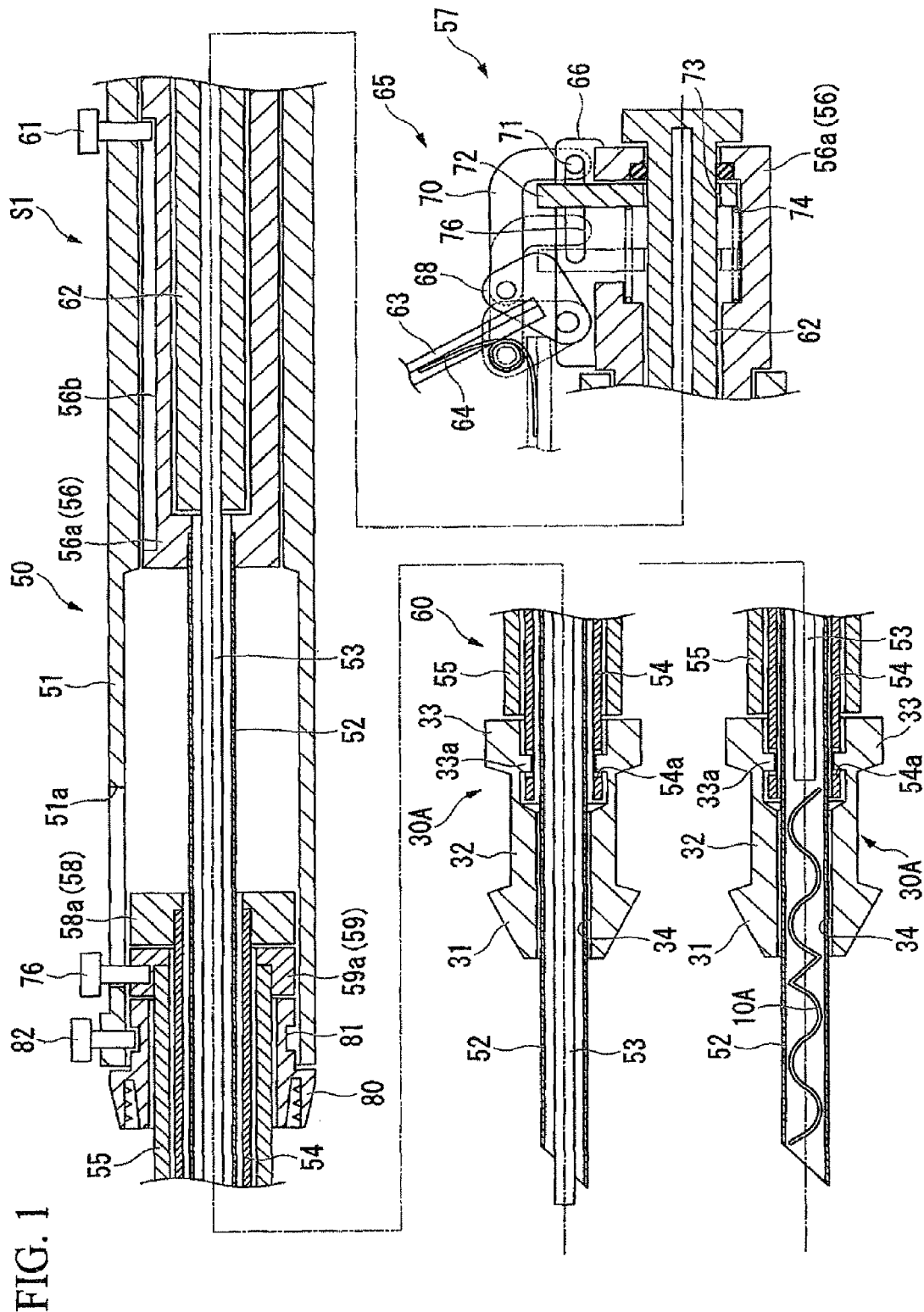
FIG. 1 shows the first embodiment of a tissue fastening apparatus of the present invention and is a cross-sectional view showing the internal structures of a tissue fastening tool, a stent and an applicator included in the apparatus.

A first embodiment according to the present invention will now be described here. As shown in FIG. 1, a tissue fastening apparatus S1 in the present embodiment is an apparatus for fixing a second biological tissue to a first biological tissue to communicate therethrough. The apparatus includes a tissue fastening tool 10A, a stent 30A and an applicator 50. Note that the first and second biological tissues are not limited to different organs. For example, a section of an organ may be referred to as the first biological tissue and a different section of the same organ may be referred to as the second biological tissue, so as to include fixing different sections within the same organ. In the present embodiment, a procedure to make a bypass between the duodenum as the first biological tissue and the common bile duct as the second biological tissue after fixing the second biological tissue to the first biological tissue is described hereunder.

Figure 2:
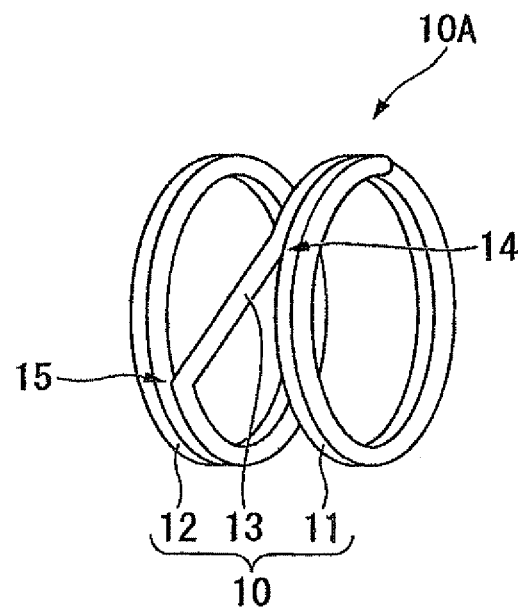
FIG. 2 is a perspective view showing the tissue fastening tool included in the tissue fastening apparatus.
Figure 3:
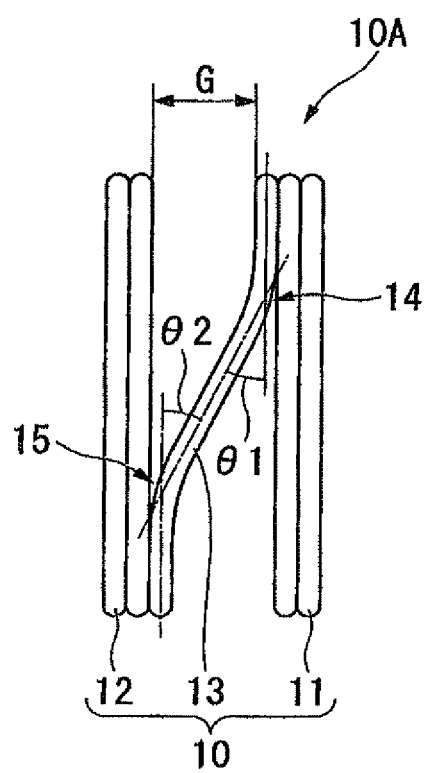
FIG. 3 is a plan view of the tissue fastening tool as seen from a different direction from the FIG. 2.

As shown in FIG. 2, a tissue fastening tool 10A is for fastening the duodenum and the common bile duct. The tissue fastening tool 10A is provided with a first tissue fixing section 11 which is hooked onto the duodenum and a second tissue fixing section 12 which is hooked onto the common bile duct adjacent to the duodenum. The tissue fastening tool 10A is further provided with the coupling section 13 which couples the first tissue fixing section 11 with the second tissue fixing section 12 therebetween. The tissue fastening tool 10A is formed of a highly-elastic element wire 10 wound into a coil shape for all sections, such as the first tissue fixing section 11, the second tissue fixing section 12 and the coupling section 13. A bending section 14 is formed in the wire disposed between the first tissue fixing section 11 and the coupling section 13. Similarly, a bending section 15 is formed in the wire disposed between the second tissue fixing section 12 and the coupling section 13. Both the first tissue fixing section 11 and the second tissue fixing section 12 are formed into a coil shape with equal diameter. A gap G is created by forming the coupling section 13 between the tissue fixing sections 11 and 12. The central axis of the coil shaped first tissue fixing section 11 is corresponds to that of the coil shaped second tissue fixing section 12. As shown in FIG. 3, the wire forming the coupling section 13 forms an angle θ1 with the wire forming the coil shaped first tissue fixing section 11 at the bending section 14. The wire forming the coupling section 13 also forms an angle θ2 with the wire forming the coil shaped second tissue fixing section 12 at the bending section 15. The size of the angle θ1 formed at the bending section 14 is substantially the same as that of the angle θ2 formed at the bending section 15.

The tissue fastening tool 10A is stretched, and one end thereof is pierced into a biological tissue. Then, one of the tissue fixing sections (for example, the second tissue fixing section 12) is penetrated through sequentially a wall of duodenum and a wall of common bile duct. The second tissue fixing section 12 penetrated through the wall of the duodenum and the wall of the common bile duct is restored to its original coil shape at the inside of the common bile duct by being removed a restraining force acted on the second tissue fixing section 12, and then is hooked onto the common bile duct. On the other hand, the first tissue fixing section 11 is restored to its original coil shape at the inside of the duodenum by being removed a restraining force acted on the first tissue fixing section 12, and then is hooked onto the duodenum. The wall of the duodenum and the wall of the common bile duct are fastened such that both walls are pressed against each other, by the first tissue fixing section 11 being hooked onto the duodenum and the second tissue fixing section 12 being hooked onto the common bile duct. The coupling section 13 is detained within both walls of the organs.

As shown in FIG. 1, the stent 30A is for penetrating through the wall of the duodenum and the wall of common bile duct fastened by the tissue fastening tool 10A. The stent 30A is provided with a dilating portion 31, an indwelled portion 32, a fall-off prevention portion 33 and a through hole 34. The dilating portion 31 forms a conical shape in which the diameter increases from a front end to substantially a rear end thereof. The indwelled portion 32 forms a columnar shape and is disposed behind of the dilating portion 31. A diameter of the indwelled portion 32 is uniform and is smaller than the maximum outer diameter of the dilating portion 31. The fall-off prevention portion 33 forms a columnar shape and is disposed behind of the indwelled portion 32. An outer diameter of the fall-off prevention portion 33 is larger than that of the indwelled portion 32. The through hole 34 passes through the dilating portion 31 the indwelled portion 32 and the fall-off prevention portion 33 in a longitudinal direction of the stent 30A.

Projections 33a which are formed so as to protrude in a radial direction of the stent 30A is disposed on an inner face of the fall-off prevention portion 33. The projections 33a are comprised of a part of a mounting section in which the stent 30A is detachably disposed on the sheath 54 of the applicator 50 to be described later.

As for the materials used to make the stent 30A may be selected from any one of or a polymer of: stainless steel (SUS), titanium (Ti), bioabsorbable magnesium, polyethylene (PE), polyetheretherketone (PEEK), polysulfone, liquid crystal polymer, polylactic acid, polyglycolic acid, polydioxanone, polyhydroxyalkanoates, and caprolactone. These materials have superb biocompatibilities to living tissues, hence there is little burden on a body while the stent 30A is indwelled in the body. In particular, polylactic acid, polyglycolic acid, polydioxanone, polyhydroxyalkanoates and caprolactone degrade over a period of time while they are indwelled in the body, and are consequently absorbed into the body. Therefore they are preferably selected since there are no foreign substances will remain in the body.

The applicator 50 is a tool to indwell the tissue fastening tool 10A and the stent 30A in the body, and is provided with an applicator main body 51, a puncturing tool 52, a stylet (fastening tool pusher) 53, a sheath 54 and a stent pusher 55 as shown in FIG. 1. The applicator main body 51 is in a cylindrical shape. The puncturing tool 52 is in a needle-like-tube shape and is used with accommodating the tissue fastening tool 10A therein. In addition, an electrode may be provided at a distal end of the puncturing tool 52, and the puncturing tool 52 may be pierced into the wall of the duodenum and the wall of the common bile duct by cauterizing the biological tissues. In this case, the distal end of the puncturing tool 52 may not have to be sharp.

The stylet 53 forms a flexible-rod shape and is inserted into the puncturing tool 52 so as to be freely advanced and retracted within the puncturing tool 52, and dispenses the tissue fastening tool 10A accommodated in the puncturing tool 52 out from the distal end of the puncturing tool 52. The puncturing tool 52 is inserted into the sheath 54 so as to be freely advanced and retracted within the sheath 54. The sheath 54 moves the stent 30A which is detachably disposed at the distal end thereof relative to the puncturing tool 52.

The tubular stent pusher 55 accommodates the sheath 54, and the sheath 54 is inserted into the stent pusher 55 so as to be freely advanced and retracted. The stent pusher 55 separates the sheath 54 from the stent 30A disposed at the distal end of the sheath 54.

The applicator main body 51 includes a puncturing tool operating section 56, a stylet operating section (fastening tool pusher operating section) 57, a sheath operating section 58 and a stent pusher operating section 59. The puncturing tool 52, the stylet 53 and the sheath 54 are flexible, and are disposed along the same axial line. They consist of an insertion section 60 which is inserted into an instrument channel of an inserting section of an endoscope, hence the insertion section 60 is longer than the instrument channel of the endoscope.

The distal end surface of the puncturing tool 52 is obliquely formed with respect to the longitudinal direction thereof. Therefore, the distal end of the puncturing tool 52 is formed so as to be incisive. A proximal end of the puncturing tool 52 is connected to the puncturing tool operating section 56 provided at a rear portion of the applicator main body 51.

The distal end of the stylet 53 is smooth, not incisive. The proximal end of the stylet 53 is connected to the stylet operating section 57 provided inside of the puncturing tool operating section 56.

A distal end surface of the sheath 54 is formed evenly in a direction perpendicular to the longitudinal direction of the sheath 54. Small holes 54a are disposed at the distal end of the sheath 54 with the same number or more of the projections 33a of the stent 30A. The small holes 54a are disposed in a peripheral direction of the sheath 54, and each of the holes penetrates through the wall of the sheath 54. The small holes 54a consist of a part of the mounting section where the stent 30A is detachably disposed to the sheath 54. When the distal end of the sheath 54 is pushed into the through hole 34 of the stent 30A from the rear end, the projections 33a each are engaged to the small holes 54a. Hence the stent 30A is attached to the distal end of the sheath 54. Due to the flexibility of the sheath 54, when the sheath 54 is pulled toward its rear direction upon detaining the stent 30A at a fixed position, the sheath 54 is elastically deformed so as to detach from the small holes 54a. Therefore, the stent 30A separates from the distal end of the sheath 54. When the stent 30A is made of elastic material, both of the sheath 54 and projections of the stent 30A are elastically deformed, thereby the stent 30 also separates from the distal end of the sheath 54.

The small holes 54a may not be limited to always penetrating through the wall of the sheath 54, the small holes may be indentations formed on the outer surface of the sheath 54. Protrusions may be formed on the sheath 54 as well as forming small holes on the stent 30A to engage therebetween.

The proximal end of the sheath 54 is connected to the sheath operating section 58 disposed at a front portion of the applicator main body 51.

A distal end surface of the stent pusher 55 is formed evenly in a direction perpendicular to the longitudinal direction of the stent pusher 55. The proximal end of the stent pusher 55 is connected to the stent pusher operating section 59 disposed at the front portion of the applicator main body 51.

The puncturing tool operating section 56 includes a cylindrical-shaped first shaft 56a inserted into the applicator main body 51 from the rear end of the applicator main body 51. An outer diameter of the first shaft 56a is slightly smaller than an inner diameter of the rear portion of the applicator main body 51. Therefore, the first shaft 56a can be slid with respect to the inner surface of the rear portion of the applicator main body 51. The proximal end of the puncturing tool 52 is fixed to the distal end of the first shaft 56a inserted into the applicator main body 51 so as to align the longitudinal direction of the puncturing tool 52 with the longitudinal direction of the first shaft 56a. The puncturing section 52 can change its position relative to the applicator main body 51 by making the first shaft 56a slide against the applicator main body 51.

A screw hole is formed in a radial direction at the rear portion the applicator main body 51, and a screw 61 is screwed into the screw hole. The distal end of the screw 61 is projected into the inner space of the applicator main body 51. On the other hand, a groove 56b is formed along the longitudinal direction of the first shaft 56a on the outer surface of the first shaft 56a. The distal end of the screw 61 is loosely arranged within the groove 56b of the first shaft 56a inserted into the applicator main body 51. Therefore, the groove 56b limits a range of movement of the first shaft 56a with respect to the applicator main body 51. The screw 61 is further screwed into the screw hole and the distal end of the screw 61 is pressed against the bottom surface of the groove 56b, and thereby it is possible to hold the first shaft 56a with respect to the applicator main body 51 at any desired position.

The stylet operating section 57 includes a cylindrical-shaped second shaft 62 inserted into the first shaft 56a from the rear end of the first shaft 56a, a lever 63 swingably supported by the first shaft 56a which also supports the puncturing tool 52, a torsion coil spring 64 which spring-biases the lever 63 to the direction in which the distal end of the lever 63 separates from the applicator main body 51, and a linkage 65 which translates the swinging motion the lever 63 into a liner motion along the puncturing tool 52 of the stylet 53.

A proximal end of the stylet 53 is inserted into the second shaft 62 from the distal end of the second shaft 62 and is fixed to the second shaft 62 so as to align the longitudinal direction of the stylet 53 with the longitudinal direction of the second shaft 62. The stylet 53 can change positions relative to the puncturing tool 52 by sliding the second shaft 62 with respect to the first shaft 56a.

The linkage 65 includes a base 66, a bracket 68, a bar 70, a plate 72 and a compression coil spring 74. The base 66 is fixed on an outside of the first shaft 56a, and the bracket 68 is pivotably supported by the base 66. A proximal end of the lever 63 is fixed to the bracket 68. One end of the bar 70 is pivotably supported by the bracket 68, and the other end of the bar 70 is pivotably supported by the base 66. A pin 71 provided at the other end of the bar 70 is loosely arranged into an elongated hole 76 formed in the base 66 along the sliding direction on the second shaft 62 of the.

A hole 73 with a diameter that is larger than the outer diameter of the second shaft 62 is formed on the plate 72, and the second shaft 62 inserted into the first shaft 56a passes through the hole 73. A difference between the outer diameter of the second shaft 62 and the inner diameter of the hole 73 is extremely small. When the plate 72 is tilted and advanced in the longitudinal direction of the second shaft 62; in other words, in the insertion direction of the second shaft 62 into the first shaft 56a, friction is exerted upon contacting the inner face of the hole 73 to the outer face of the second shaft 62. Therefore, a force applied to the plate 72 is translated and exerted on the second shaft 62.

The compression coil spring 74 is disposed within the first shaft 56a, and biases the plate 72 to a direction opposite to the insertion direction of the second shaft 62 into the first shaft 56a.

When the lever 63 is moved toward the applicator main body 51, one end of the bar 70 is pulled toward the front portion of the applicator main body 51 via the bracket 68, and the other end of the bar 70 is moved along the long hole 76. The plate 72 is pushed by the other end of the bar 70, and is advanced to the insertion direction of the second shaft 62 into the first shaft 56a against a reaction of the compression coil spring 74. At this time, the plate 72 is slightly tilted, and then friction occurs between the plate 72 and the second shaft 62. Therefore, a force applied to the plate 72 is translated and exerted to the second shaft 62, and thereby the second shaft 62 is pushed into the first shaft 56a. When the lever 63 is released, the torsion coil spring 64 separates the distal end of the lever 63 from the applicator main body 51, and the compression coil spring 74 pushes the plate 72 back to the initial position without creating friction between the second shaft 62 and the plate 72.

Since the moving distance of the other end of the bar 70 per one operation on the lever 63 is always uniform, an insertion length of the second shaft 62 into the first shaft 56a per operation on the lever 63 is also uniform. Therefore, it is possible to control the insertion length of the second shaft 62 into the first shaft 56a as per number of operations on the lever 63. That is, the insertion length of the stylet 53 into the puncturing tool 52 as per number of operations on the lever 63 can be controlled. This mechanism indicates that the length of the tissue fastening tool 10A dispensed from the distal end of the puncturing tool 52 is controlled as per the number of operations on the lever 63.

When the tissue fastening tool 10A forms the coil shape as described in this embodiment, the insertion length of the stylet 53 per operation on the lever 63 is preferred to be substantially n or 1/n times (n is a positive integer) the circumference of the tissue fastening tool 10A. For example, if the insertion length of the stylet 53 per operation on the lever 63 is substantially equal to the circumference of the tissue fastening tool 10A, the tissue fastening tool 10A is dispensed from the distal end of the puncturing tool 52 by one reel length every time the lever 63 is operated once. Furthermore, if the second tissue fixing section 12 consists of two reel lengths of the tissue fastening tool 10A, only the second tissue fixing section 12 can be dispensed from the distal end of the puncturing tool 52 by operating the lever 63 twice. Alternatively, if an insertion length of the stylet 53 per operation on the lever 63 is substantially equal to a half of the circumference of the tissue fastening tool 10A, the tissue fastening tool 10A is dispensed from the distal end of the puncturing tool 52 by a half reel length every time the lever 63 is operated once. Furthermore, if the second tissue fixing section 12 consists of two reel lengths of the tissue fastening tool 10A, only the second tissue fixing section 12 can be dispensed from the distal end of the puncturing tool 52 by operating the lever 63 four times.

The sheath operating section 58 includes a first ring member 58a disposed inside of the applicator main body 51 so that the puncturing tool 52 is inserted into a hole of the first ring member 58a. An outer diameter of the first ring member 58a is slightly smaller than the internal diameter of the front portion of the applicator main body 51 and the internal diameter of the first ring member 58a is substantially equal to the internal diameter of the sheath 54. Therefore, the first ring member 58a can be slid with respect to the internal surface of the front portion of the applicator main body 51. The distal end of the sheath 54 is fixed to the front face of the first ring member 58a so as to align the center of the sheath 45 with that of the first ring member 58a. The sheath 54 can change its position relative to the applicator main body 51 by sliding the first ring member 58a with respect to the applicator main body 51.

The stent pusher operating section 59 includes a second ring member 59a disposed at, in particular, the front portion of the first ring member 58a in the applicator main body 51. The sheath 54 is inserted into a hole of the second ring member 59a. The outer diameter of the second ring member 59a is slightly smaller than the internal diameter of the front portion of the applicator main body 51, and the internal diameter of the second ring member 59a is substantially equal to the internal diameter of the tubular stent pusher 55. Thus the second ring member 59a is disposed in a slidable manner with respect to the inner surface of the front portion of the applicator main body 51. The proximal end of the stent pusher 55 is fixed to a front face of the second ring member 59a so as to align the center of the stent pusher 55 with that of the second ring member 59a. The stent pusher 55 can change its position relative to the applicator main body 51 by sliding the second ring member 59a relative to the applicator main body 51.

As shown in FIG. 1, a screw hole is formed on an outer side of the second ring member 59a in a radial direction of the second ring member 59a. On the other hand, an elongated hole 51a is formed at the front portion of the applicator main body 51 along the sliding direction of the second ring member 59a. An screw 76 is screwed into the screw hole on the second ring member 59a through the long hole 51a. Therefore, the long hole 51a limits a range of movement of the second ring member 59a with respect to the applicator main body 51. When the screw 76 is further screwed into the screw hole and then the head portion of the screw is pressed onto the applicator main body 51, it is possible to hold the second ring member 59a with respect to the applicator main body 51 at any desired position.

Figure 4:
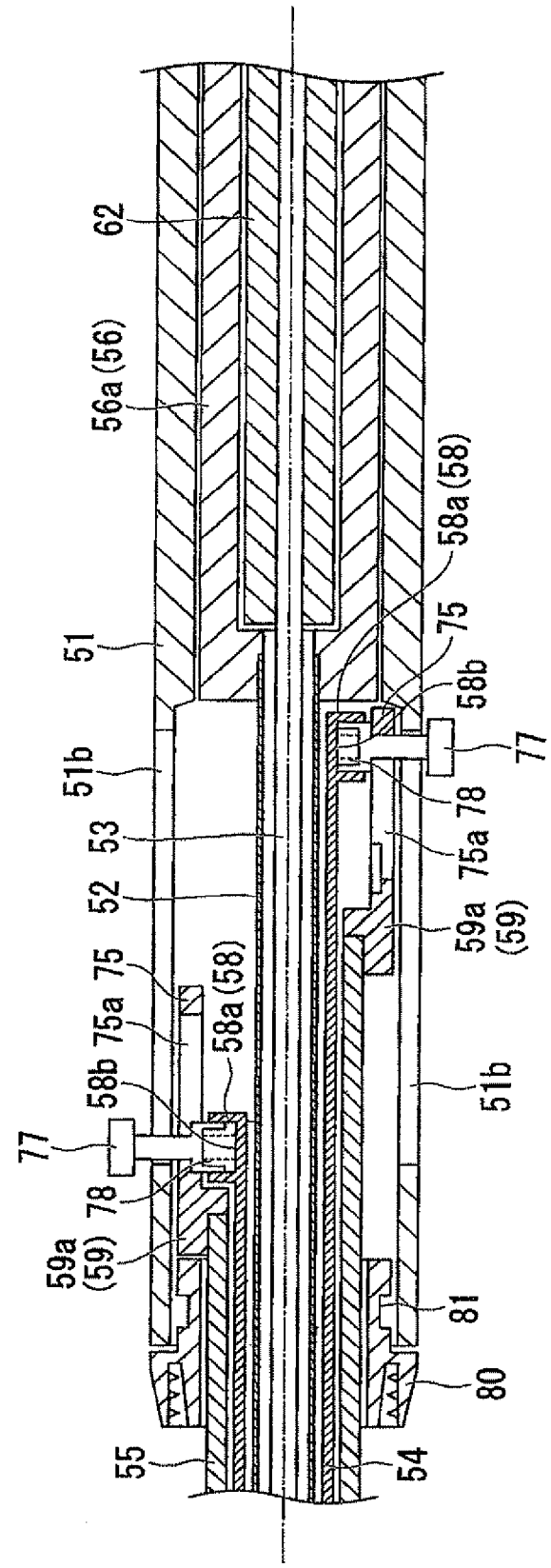
FIG. 4 shows a constitution of the first and the second ring members disposed in the applicator within the apparatus, the upper half shows a state in which the first and the second ring members are moved to the front end of the applicator, and the lower half shows a state in which the first and the second ring members are moved to the rear end of the applicator.

As shown in FIG. 4, two recessed portions 58b are formed on the outer side of the first ring member 58a. On the other hand, two bars 75 projected to the rear side are disposed at the second ring member 59a. Elongated holes 75a are respectively formed in the two bars 75 along the sliding direction of the first ring member 58a relative to the applicator main body 51. Further, two elongated holes 51b are formed in the applicator main body 51 so as to be parallel to the long hole 75a.

Two pins 77 are inserted into each of the two recessed portions 58b of the first ring member 58a by passing through the elongated holes 51b of the applicator main body 51 and the elongated hole 75a of the second ring member 59a. Therefore, the long hole 75a limits a range of movement of the first ring member 58a with respect to the second ring member 59a. Moreover, since the second ring member 59a is slidable relative to the applicator main body 51, the elongated holes 51b are formed so as to be longer than a length of the long hole 75a due to the range of movement of the second ring member 59a and that of the first ring member 58a.

Figure 5:
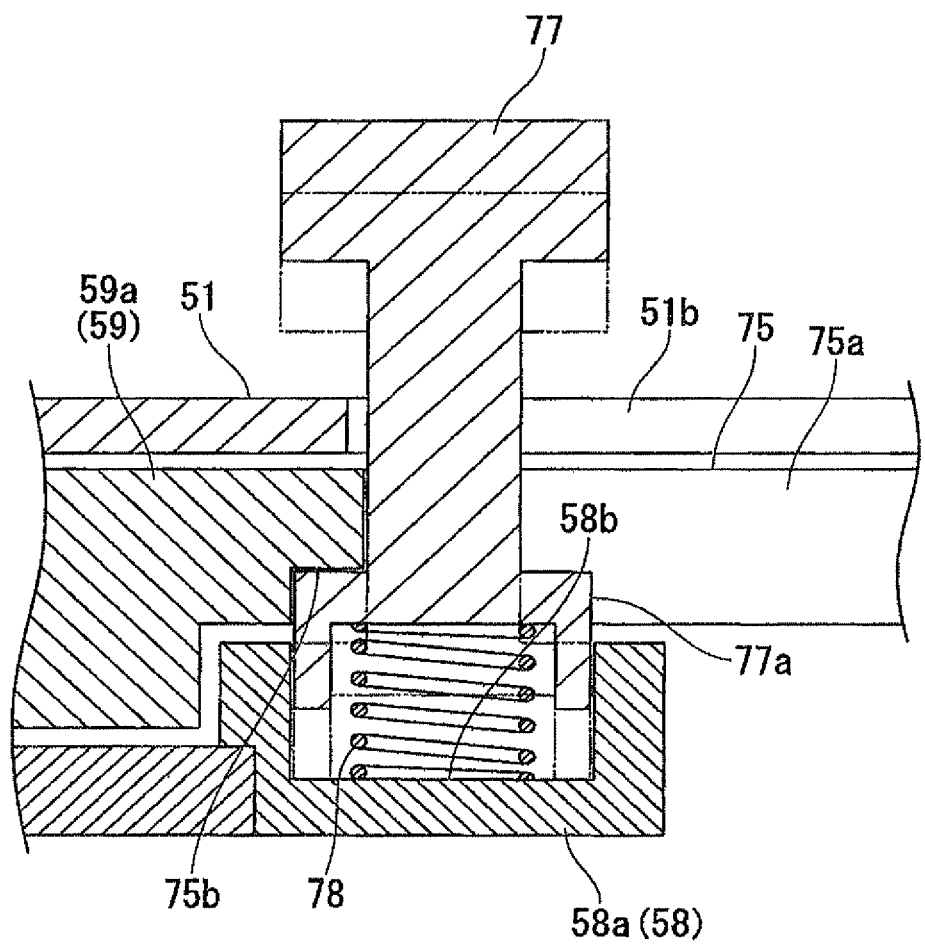
FIG. 5 is a cross-sectional view showing the structure of a pin to restrain the first ring member on the second ring member.

As shown in FIG. 5, a compression spring 78 is disposed between the recessed portion 58b and a distal end of the pin 77. Therefore, the pin 77 is always biased outward the radial direction of the second ring member 59a. A recessed portion 75b is formed in the bar 75. When the first ring member 58a is disposed in the vicinity of the front face of the second ring member 59a, a large-diameter portion 77a of the pin 77 is fitted to the recessed portion 75b.

When the first ring member 58a is disposed in the vicinity of the front face of the second ring member 59a, the large-diameter portion 77a of the pin 77 is fitted to the recessed portion 75b, hence the first ring member 58a is restrained by the second ring member 59a via the pin 77. When the pin 77 is pushed into the applicator main body 51 against the bias force of the compression spring 78, the large-diameter portion 77a of the pin 77 is removed from the recessed portion 75b, hence the first ring member 58a is released from the second ring member 59a so as to move toward the rear portion of the applicator main body 51. Therefore, it is possible to shift the sheath 54 to the proximal side with respect to the stent pusher 55.

A connector 80 is fitted to the distal end of the applicator main body 51. An inside screw is formed in the connector 80 so as to fix the applicator 50 on the endoscope 2 by screwing the inside screw into the connector 80 of the endoscope 2. A groove 81 is formed on the outside of the connector 80 along a periphery direction. On the other hand, a screw hole is formed on the applicator main body 51 in the radial direction, and a screw 82 is screwed into the screw hole. A distal end of the screw 82 is protruded inside of the applicator main body 51. The distal end of the screw 82 is loosely arranged in the groove 81 of the connector 80. Therefore, it is possible to freely rotate the applicator main body 51 relative to the connector 80 fixed to the endoscope 2. When the screw 82 is further screwed into the screw hole and the distal end of the screw 82 is pressed onto the bottom of the groove 81, it is possible to hold the applicator main body 51 with respect to the connector 80 at any desired position.

Figure 6:
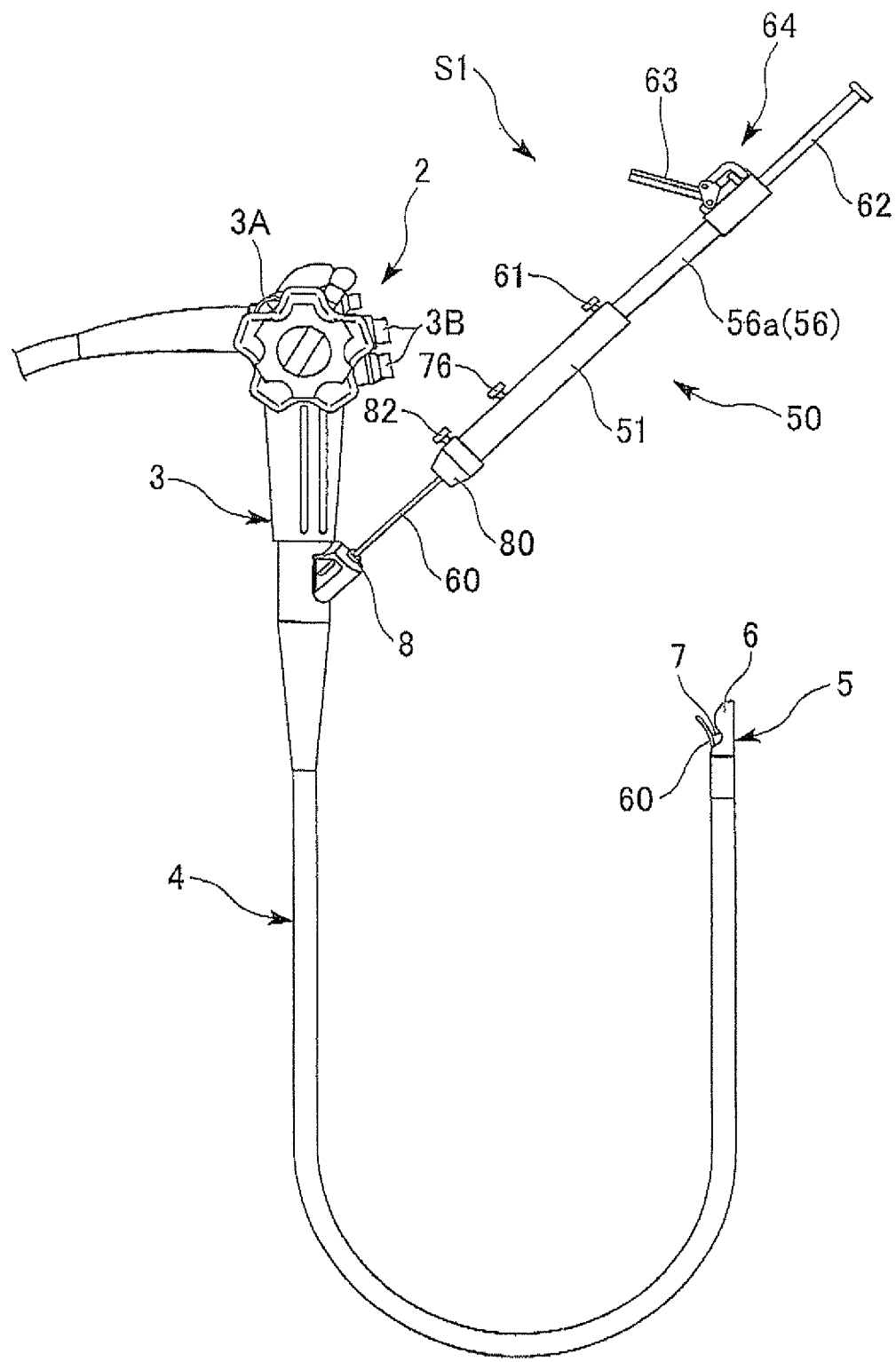
FIG. 6 shows a state in which an insertion section of the applicator is inserted into the instrument channel of the endoscope.

FIG. 6 shows the linear scanning type ultrasonic endoscope as the endoscope 2 used together with the tissue fastening apparatus S1. The endoscope 2 is provided with a flexible insertion portion 4 that extends from the operation part 3 used outside the body. A knob 3A for bending the front end part of the insertion portion 4 into a curved shape and various buttons 3B are provided in the operation part 3. A cover 5 is attached to a distal end of the insertion portion 4. An ultrasonic probe 6 is attached to the cover 5. The ultrasonic probe 6 is placed on the flat plane passed through the axial line of the insertion portion 4. Ultrasonic transducers are disposed along the periphery of the circular arc shape of the ultrasonic probe 6. Furthermore, the endoscope 2 is provided with a forceps elevator 7 for delivery of the distal end portion of the applicator 50 in the lateral direction. The delivery direction of the insertion section 60 of the applicator 50 from the distal end of the insertion portion 4 can be adjusted by operating the forceps elevator 7 at the proximal side of the endoscope 2. The endoscope 2 may be provided with an ultrasonic probe of different types. Moreover, an endoscope not provided with the ultrasonic probe 6 may also be used. In this case, an ultrasonic probe used outside the body, an X-ray device, a magnetic resonance imaging (MRI) device, or a computerizing tomography (CT) device may be used jointly.

Figure 7:
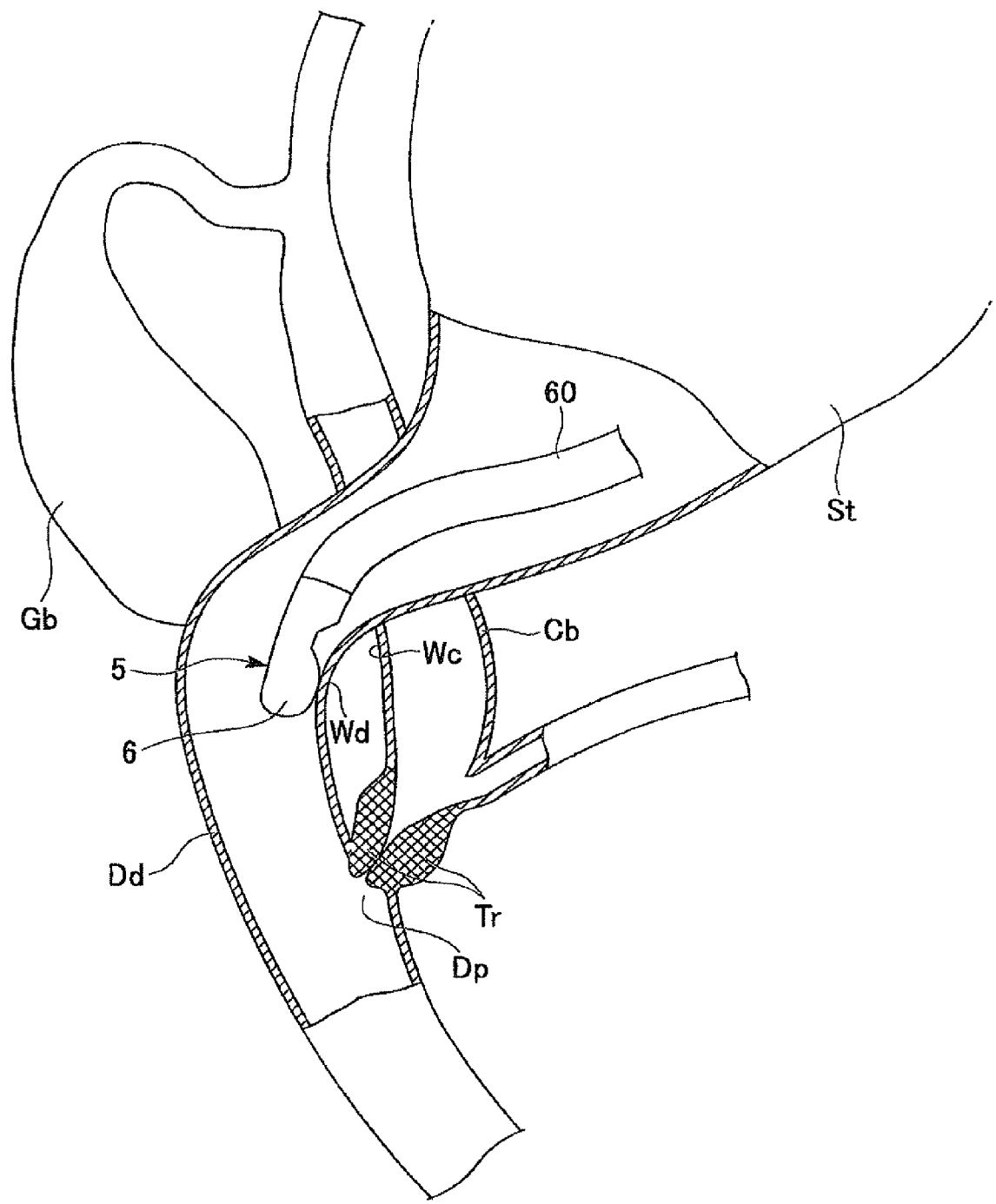
FIG. 7 shows a state in which the insertion section of the endoscope is inserted into the duodenum.

Next, the procedure to make a bypass between the common bile duct and the duodenum after joining them using the tissue fastening apparatus S1 as described above will be explained below. As shown in FIG. 7, this kind of procedure is performed when the duodenal papilla Dp is obstructed by a tumor Tr preventing bile drainage, consequently the bile assimilates in the blood causing jaundice. This procedure enables the direct drainage of bile from the common bile duct Cb to the duodenum Dd.

First, the insertion portion 4 of the endoscope 2 is inserted from the patient's mouth. The endoscope 2 is inserted into the duodenum Dd, which is the upper alimentary tact. The condition outside the duodenum Dd is examined by the ultrasonic probe 6, and an appropriate location proximally with respect to the common bile duct Cb for the procedure is searched in the area vicinity to the stomach St side with respect to the duodenal papilla Dp.

Figure 8:
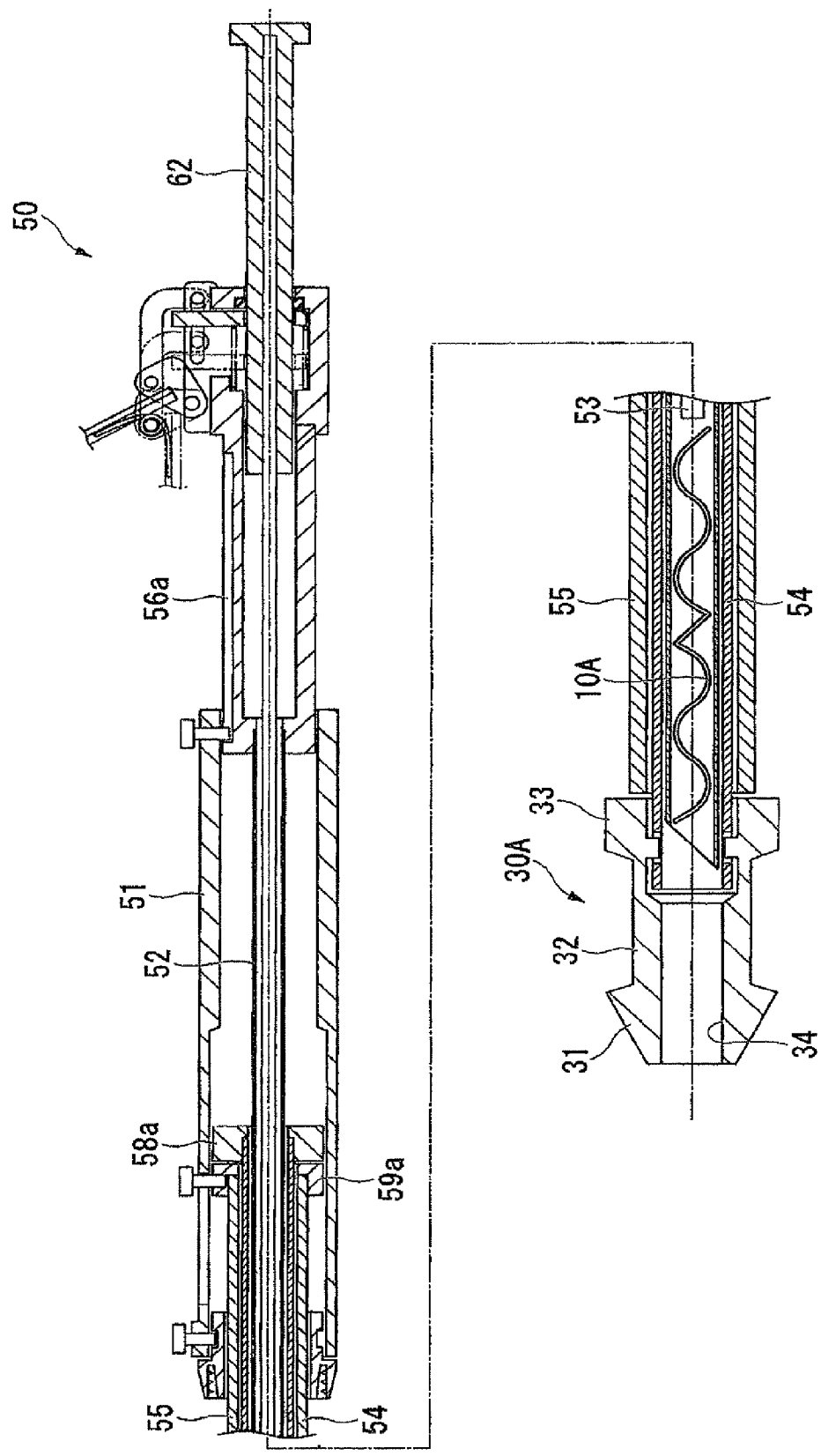
FIG. 8 through FIG. 14 are cross-sectional diagrams showing states of the applicator in use at each step upon performing a bypass procedure between the common bile duct and the duodenum, after fixing the common bile duct to the duodenum.

As shown in FIG. 8, in the applicator 50, the puncturing tool 52 is previously retracted relative to the applicator main body 51 by operating the first shaft 56a. Also, the stylet 53 is previously retracted relative to the applicator main body 51 by operating the second shaft 62. Further, the sheath 54 and the stent pusher 55 are also retracted relative to the applicator main body 51 by simultaneous operation of the first ring member 58a and the second ring member 59a. The first ring member 58a should be placed in the vicinity of the second ring member 59a. At this state, the puncturing tool 52 which accommodates the tissue fastening tool 10A therein is retracted inside of the sheath 54 until the distal end of the puncturing tool 52 is positioned in the stent 30A.

The insertion section 60 of the applicator 50 is inserted into an instrument channel of the endoscope 2 and advanced therethrough, and then the applicator 50 is fixed to the endoscope 2. Therefore, the distal end of the insertion section 60 is protruded from the distal end of the insertion portion 4 of the endoscope 2. The protruding direction of the insertion portion 60 from the distal end of the insertion portion 4 can be adjusted by the forceps elevator 7.

Figure 9:
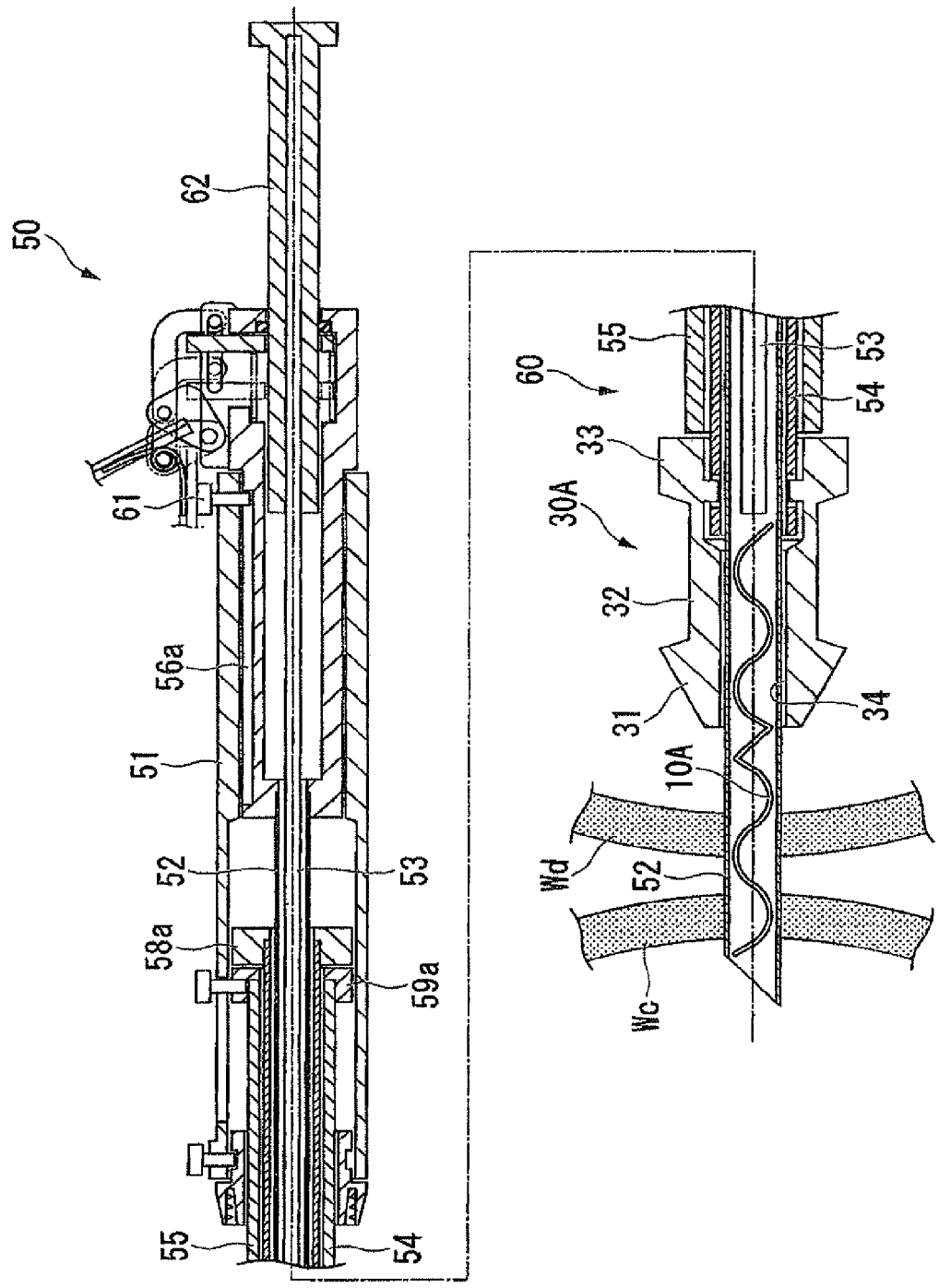

The common bile duct Cb is observed using the ultrasonic probe 6 attached to the endoscope 2 through the duodenum Dd, and the position in which the puncturing tool 52 will be pierced into the common bile duct Cb is determined. As shown in FIG. 9, after the screw 61 is loosened, the first shaft 56a is pushed into the applicator main body 51, and thereby the distal end of the puncturing tool 52 is protruded from the distal end of the stent 30A attached to the distal end of the sheath 54. Therefore, a sharp distal end of the puncturing tool 52 pierces the wall Wd of the duodenum Dd from the inside of the duodenum Dd to the outside, and then pierces the wall Wc of the common bile duct Cb from the outside of the common bile duct Cb to the inside. Then, the screw 61 is tightened to fix the first shaft 56a to the applicator main body 51.

Figure 10:
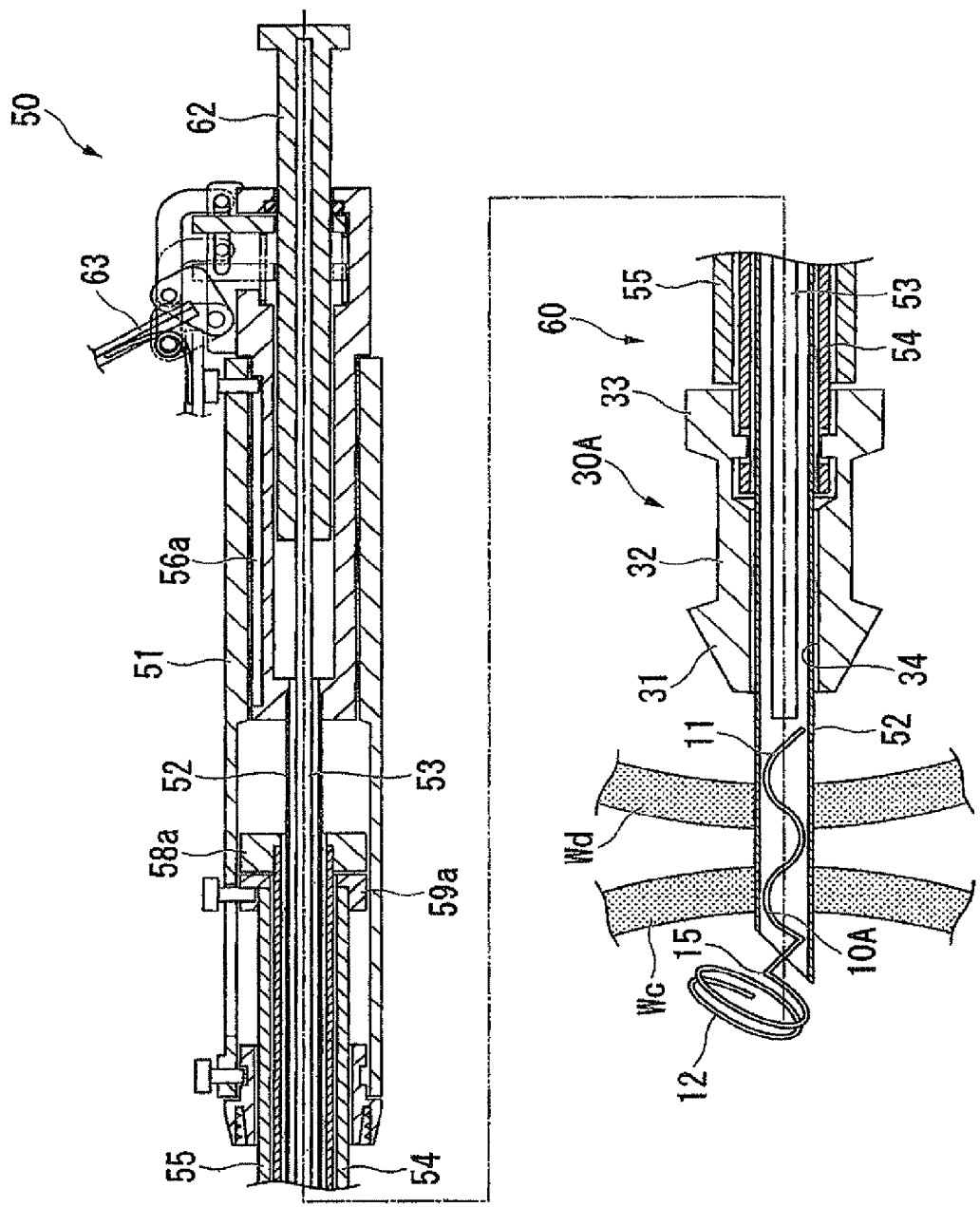

As shown in FIG. 10, the lever 63 is operated to push the second shaft 62 into the first shaft 56a by a predetermined length. For example, when the lever 63 is operated by predetermined times. Therefore, the stylet 53 changes its position relative to the puncturing tool 52 and the second tissue fixing section 12 of the tissue fastening tool 10A is pushed out from the distal end of the puncturing tool 52. When the second tissue fixing section 12 is pushed out from the puncturing tool 52, the second tissue fixing section 12 is restored to its original coil shape and is hooked onto the inside surface of the wall We of the common bile duct Cb.

After the screw 61 is loosened, the first shaft 56a is slightly pulled out from the applicator main body 51, and thereby the protruded amount of the puncturing tool 52 from the distal end of the stent 30A is reduced. Then, the screw 61 is tightened to fix the first shaft 56a to the applicator main body 51. Therefore, the distal end of the puncturing tool 52 slightly separates from the inside surface of the wall Wd of the duodenum Dd.

Figure 11:
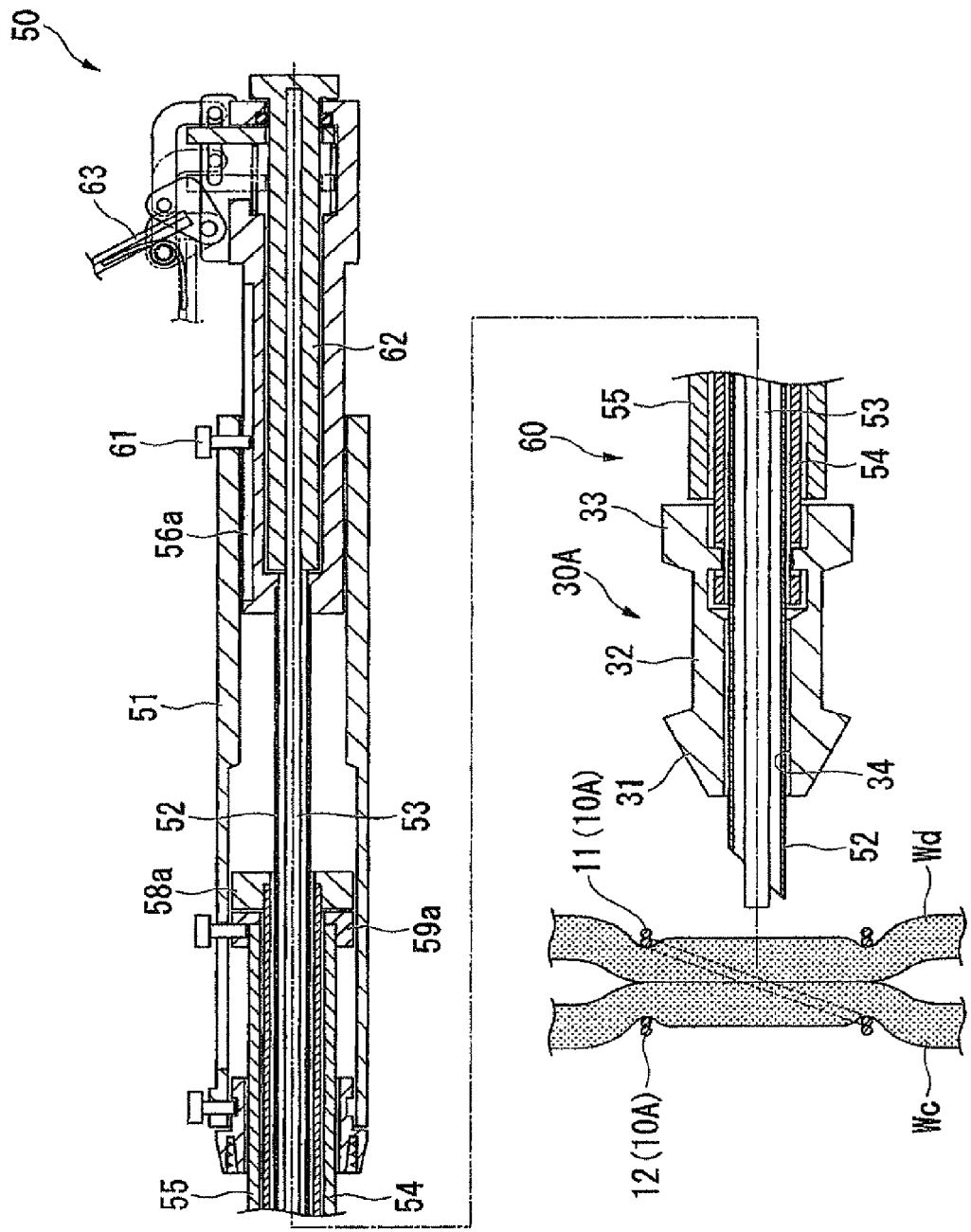

As shown in FIG. 11, the lever 63 is re-operated to push the second shaft 62 into the first shaft 56a by a predetermined length. For example, the lever 63 is operated at predetermined times. Therefore, the stylet 53 changes its position relative to the puncturing tool 52 and the coupling section 13 and the first tissue fixing section 11 of the tissue fastening tool 10A are pushed out form the distal end of the puncturing tool 52. When the first tissue fixing section 11 is pushed out from the puncturing tool 52, the first tissue fixing section 11 is restored to its original coil shape and is hooked onto the inner side of the wall Wd of the duodenum Dd.

When the tissue fastening tool 10A is pushed out from the puncturing tool 52, the tissue fastening tool 10A fastens the duodenum Dd and the common bile duct Cb by clamping the wall Wd of the duodenum Dd hooked by the first tissue fixing section 11 and the wall Wc of the common bile duct Cb hooked by the second tissue fixing section 12.

Figure 12:
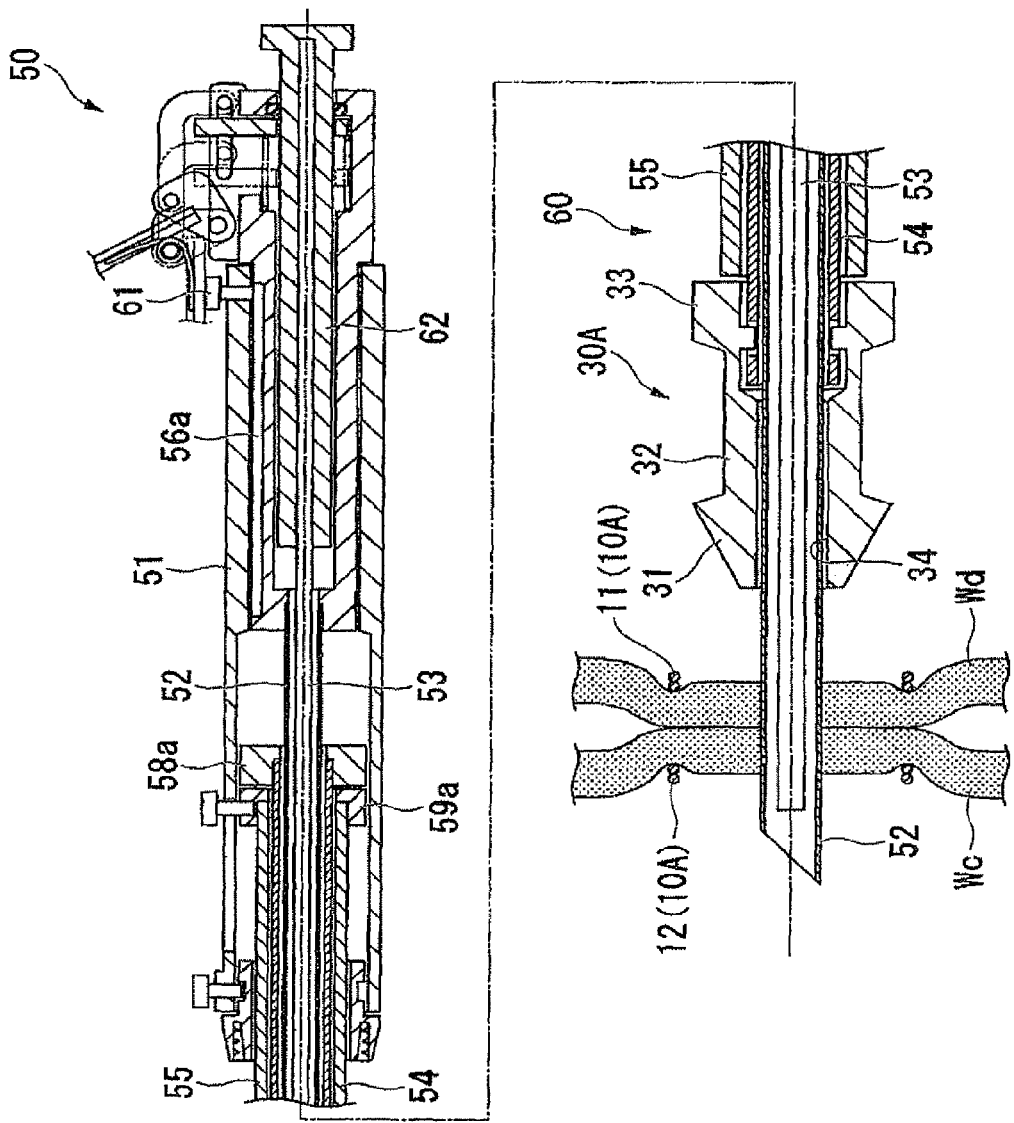

As shown in FIG. 12, the second shaft 62 is slightly retracted to accommodate the distal end of the stylet 53 within the puncturing tool 52. Then, after the screw 61 is loosened, the first shaft 56a is re-pushed into the applicator main body 51, and thereby the distal end of the puncturing tool 52 is protruded from the distal end of the stent 30A. Therefore, the sharp distal end of the puncturing tool 52 pierces an area of the wall Wd of the duodenum Dd and the wall Wc of the common bile duct Cb surrounded by the tissue fastening tool 10A. Then, the screw 61 is tightened to fix the first shaft 56a to the applicator main body 51, and the lever 63 is operated to completely push the second shaft 62 into the first shaft 56a. Therefore, since the smooth distal end of the stylet 53 protrudes from the sharp distal end of the puncturing tool 52, damage to the peripheral tissues by the sharp distal end of the puncturing tool 52 can be prevented.

Figure 13:
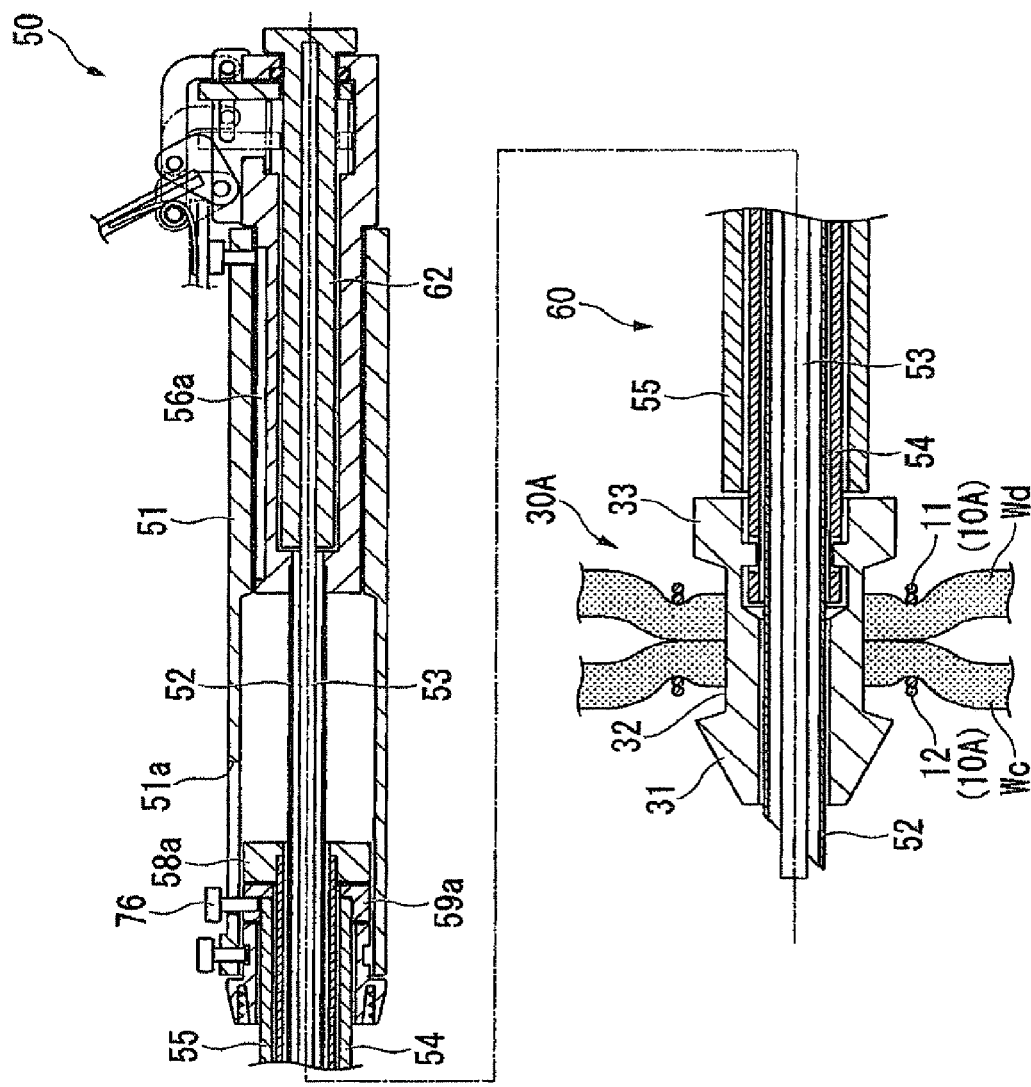

As shown in FIG. 13, after the screw 76 is loosened, the first ring member 58a and the second ring member 59a are advanced toward the distal end of the applicator main body 51. Therefore, in a state where the sheath 54 and the stent pusher 55 is fixed to the applicator main body 51 through the first shaft 56a, the position of the sheath 54 and the stent pusher 55 relative to the puncturing tool 52 shifts, and thereby the stent 30A is pushed along the puncturing tool 52. The dilating portion 31 of the stent 30A pierces the area of the wall Wd of the duodenum Dd and the wall Wc of the common bile duct Cb surrounded by the tissue fastening tool 101A so as to expand the perforation previously formed by the puncturing tool 52. When the dilating portion 31 penetrates through the wall Wd of the duodenum Dd and the wall Wc of the common bile duct Cb, the stent 30A is indwelled between the wall Wd of the duodenum Dd and the wall Wc of the common bile duct Cb in a state where the indwelled portion 32 is placed between the wall Wd and the wall Wc, the dilating portion 31 is protruded the inside of the common bile duct Cb, and the fall-off prevention portion 33 is detained inside of the duodenum Dd. After the stent 30A is indwelled, the screw 76 is tightened to fix the second ring member 59a to the applicator main body 51.

Figure 14:
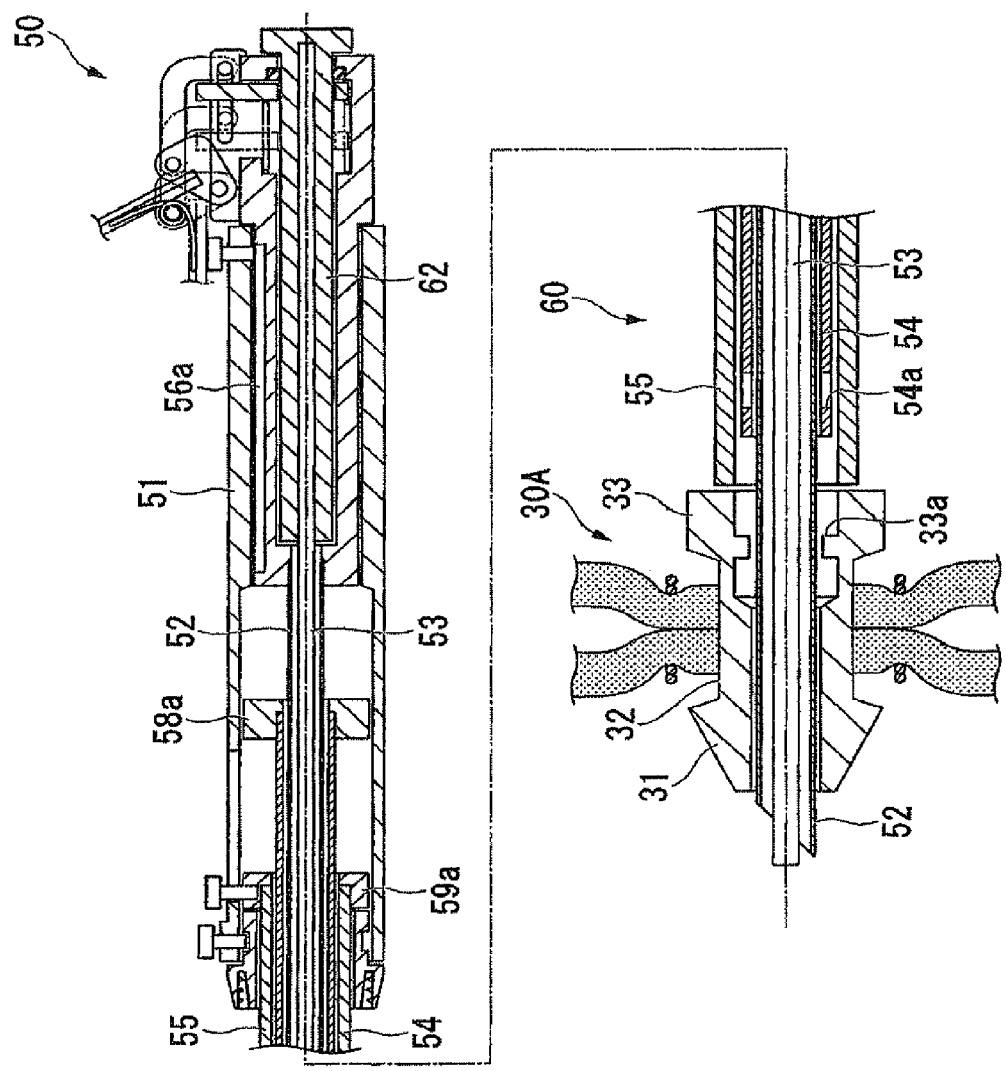

As shown in FIG. 14, while the pins 77 shown in FIG. 4 are pushed into the applicator main body 51, the first ring member 58a is retracted toward the rear end of the applicator main body 51. At this time, since the second ring member 59a is fixed to the applicator main body 51, the position of the sheath 54 relative to the stent pusher 55 shifts, and thereby the sheath 54 is pulled toward the proximal side of the endoscope. However, since the stent 30A contacts the distal end surface of the stent pusher 55, a force to resist movement acts on the stent 30A. Therefore, the distal end of the sheath 54 is elastically deformed, and thereby the projections 33a of the stent 30A are removed from the small holes 54a of the sheath 54. When the projections 33a are removed from the small holes 54a, the distal end of the sheath 54 is retracted into the stent pusher 55. Therefore, the stent 30A separates from the distal end of the insertion section 60 of the applicator 50.

After the screw 61 is loosened, the first shaft 56a is retracted from the applicator main body 51, and thereby the distal end of the puncturing tool 52 is retracted into the distal end of the sheath 54. Then, the screw 61 is tightened to fix the first shaft 56a to the applicator main body 51, and thereafter the applicator 50 is detached from the endoscope 2. In this manner, the procedures of fastening the wall Wd of the duodenum Dd and the wall Wc of the common bile duct Cb by the tissue fastening tool 10A, and indwelling the stent 30A in the wall Wd of the duodenum Dd and the wall Wc of the common bile duct Cb are completed. By virtue of the above described procedures, the duodenum Dd and the common bile duct Cb are joined through the through hole 34 of the stent 30A, consequently bile flows from the common bile duct Cb into the duodenum Dd.

When the tissue fastening tool 10A is indwelled inside of the body, the wall Wd of the duodenum Dd and the wall Wc of the common bile duct Cb are compressed by the tissue fastening tool 10A, and thereby the tissue of the area surrounded by the tissue fastening tool 10A becomes ischemic condition. When the ischemic condition is prolonged, the tissue within the area fastened by the tissue fastening tool 10A becomes necrotized. On the other hand, the walls Wd and Wc coalesce and join with each other all around at the outer periphery of the tissue fastening too 10A. As a result, the necrotized tissue falls off from the walls Wd and We along with the tissue fastening tool 10A and the stent 30A. The tissue fastening tool 10A and the stent 30A are later discharged. An anastomosis hole is formed between the walls Wd and Wc after the necrotized tissue falls off. The duodenum Dd and the common bile duct Cb are joined through the anastomosis hole, hence bile flows from the common bile duct Cb into the duodenum Dd. Since the portion all around the anastomosis hole communicating the duodenum Dd with the common bile duct Cb has coalesced, there is no concern of bile leaking out from between the walls Wd and Wc into the abdominal cavity.

According to the applicator 50, the tissue fastening tool 10A can be pushed out from the puncturing tool 52 easily with high precision by simply operating the lever 63 even with the application of a small force. In addition, the stent 30A can be separated from the distal end of the sheath 54 in a timely manner. As a result, the tissue fastening tool 10A and the stent 30A can be indwelled at any desired position within the body.

Furthermore, according to the applicator 50, when the stent 30A is pressed against the wall Wd of the duodenum wall Dd and the wall Wc of the common bile duct Cb using the sheath 54 and the stent pusher 55, the puncturing tool 52 is maintained in its predetermined position so as to prevent unnecessary damage to organs, hence safe operation is ensured.

Next, a behavior of the tissue fastening tool 10A which is protruded from the distal end of the puncturing tool 52 will be explained.

First, the tissue fastening tool 10A is dispensed from the distal end of the puncturing tool 52 which has penetrated through the wall Wd of the duodenum Dd and the wall Wc of the common bile duct Cb so that only the second tissue fixing section 12 protrudes from the distal end of the puncturing tool 52. While the second tissue fixing section 12 is pushed out from the distal end of the puncturing tool 52, the second tissue fixing section 12 is restored to its original coil shape and is hooked onto the wall Wc of the common bile duct Cb.

While the second tissue fixing section 12 is pushed out from the distal end of the puncturing tool 52, a force in which to restore into the original coil shape is generated on the second tissue fixing section 12. By exerting the force on the wall Wc of the common bile duct Cb, the tissue fastening tool 10A may be pulled into the common bile duct Cb by more than the dispensing length by the stylet 53. However, the coupling section 13 is provided between the first tissue fixing section 11 and the second tissue fixing section 12, and the bending section 15 is provided between the second tissue fixing section 12 and the coupling section 13. Therefore, once the second tissue fixing section 12 is completely pushed out from the distal end of the puncturing tool 52, as shown in FIG. 10, the path of the second tissue fixing section 12 changes so as to be different from the past. This is because once the bending section 15 of the tissue fastening tool 10A is pushed out from the distal end of the puncturing tool 52, the second tissue fixing section 12 in which the restraint has been released changes its direction depending on the angle of the bending section 15. When the direction of the second tissue fixing section 12 is changed, even if the self-restoring force into its original coil shape is generated by the second tissue fixing section 12, the force does not act onto the wall Wc of the common bile duct Cb; thus the tissue fastening tool 10A will not be pulled into the common bile duct Cb by more than the throughout length by the stylet 53.

Then, the remaining portion of the first tissue fixing section 11 of the tissue fastening tool 10A is completely pushed out from the distal end of the puncturing tool 52 which is projected out from the wall Wd of the duodenum Dd and the wall Wc of the common bile duct Cb. While the first tissue fixing section 11 is pushed out from the distal end of the puncturing tool 52, the first tissue fixing section 11 is restored to its original coil shape and is hooked onto the wall Wd of the duodenum Dd.

The first tissue fixing section 11 is hooked onto the wall Wd of the duodenum Dd and the second tissue fixing section 12 is hooked onto the wall Wc of the Common bile duct Cd, and thereby the wall Wd and the wall Wc are fastened. The coupling section 13 is detained within the duodenum wall Wd and the common bile duct wall Wc fastened by the tissue fastening tool 10A. Since the gap G is provided between the first tissue fixing section 11 and the second tissue fixing section 12, the walls Wd and Wc are fastened such that they are pressed against each other with equal force.

The angle $\theta 1$ formed between the first tissue fixing section 11 and the coupling section 13 and the angle $\theta 2$ formed between the second tissue fixing section 12 and the coupling section 13 are preferred to be less than or equal to 45 degrees (refer to FIG. 3). If the angles $\theta 1$ and $\theta 2$ are greater than 45 degrees, a strong friction force will be generated upon pushing the tissue fastening tool 10A out from the distal end of the puncturing tool 52 because at lease one of the bending section 14 forming the angle $\theta 1$ and the bending section 15 forming the angle $\theta 2$ will come into contact with the inside of the puncturing tool 52. Therefore, it may be difficult to smoothly push the tissue fastening tool 10A out from the puncturing tool 52.

The size of the gap G between the first tissue fixing section 11 and the second tissue fixing section 12 may preferably be less than or equal to 15 mm. If the size of the gap G is less than or equal to 15 mm, biological tissues of almost all organs accessible by the endoscope 2 can be fixed to each other using the applicator 50.

A plurality of types of the tissue fastening tools 10A with various sizes of the gaps G are provided in order to suit various thicknesses of target organs and characteristics of individual patients. By selecting suitable tissue fastening tools, suitable treatments can be performed for different conditions.

Figure 15:
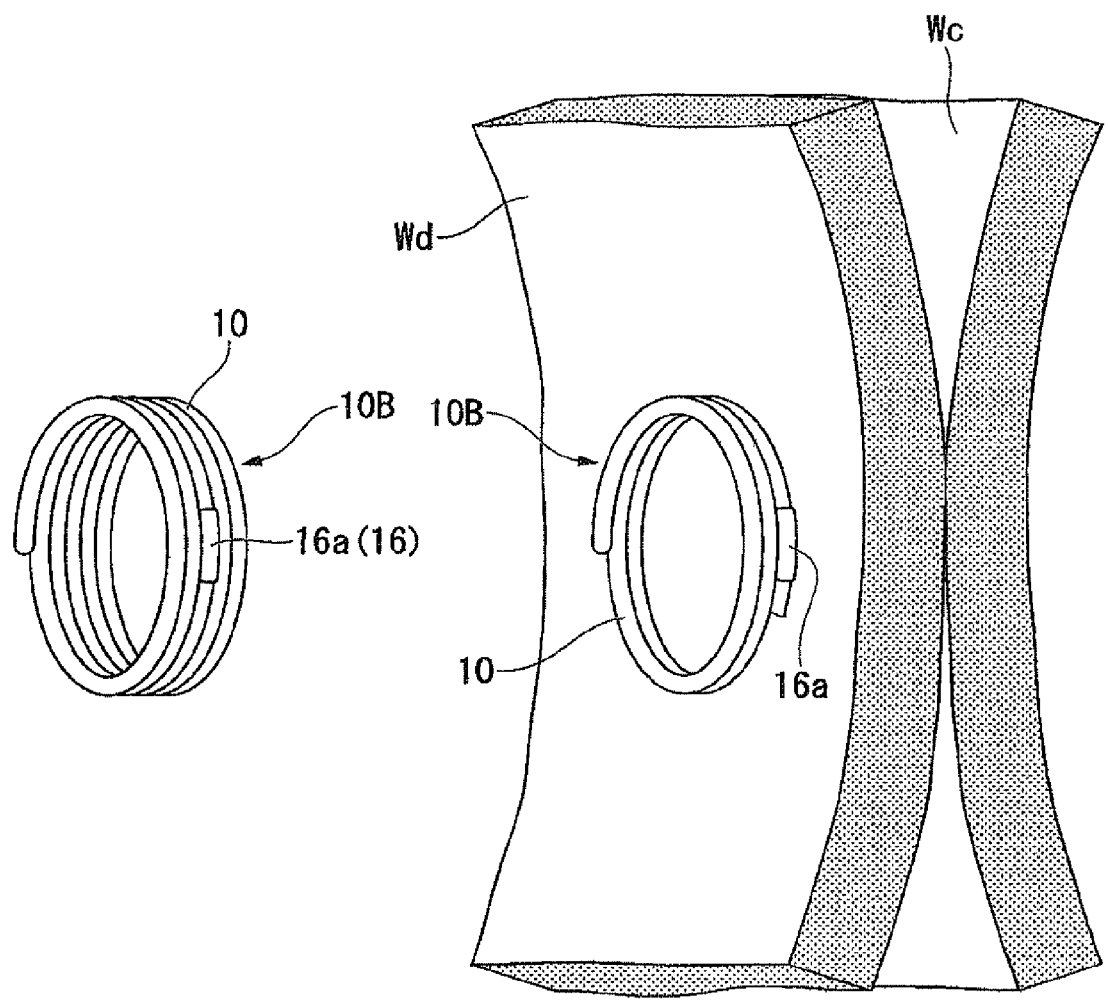
FIGS. 15 to 24 are external views showing modification examples of the tissue fastening tools.

The structure of the tissue fastening tools is not limited to the above described features. For example, as shown in FIG. 15, a tissue fastening tool 10B is provided with an anchor 16 which is disposed between the first tissue fixing section 11 and the second tissue fixing section 12 so as to separate from a main body of the tissue fastening tool 10B (which is the wire 10). The anchor 16 is a tubular member 16a in which a diameter thereof is larger than that of the main body of the tissue fastening tools 10B. The wire 10 is inserted through the anchor 16, and is disposed between the first tissue fixing section 11 and the second tissue fixing section 12. Thereafter, the anchor 16 is fixed to the wire 16 by adhesive filled into the anchor 16. The anchor 16 contacts the wall Wd of the duodenum Dd, and thereby it is prevented the tissue fastening tools 10B being pulled into the common bile duct Cb.

Alternatively, a tubular member 16a may be formed of plastic deformable materials such as metals so that the tubular member 16a is fixed to the wire 10 by caulking the tubular member 16a.

Figure 16:
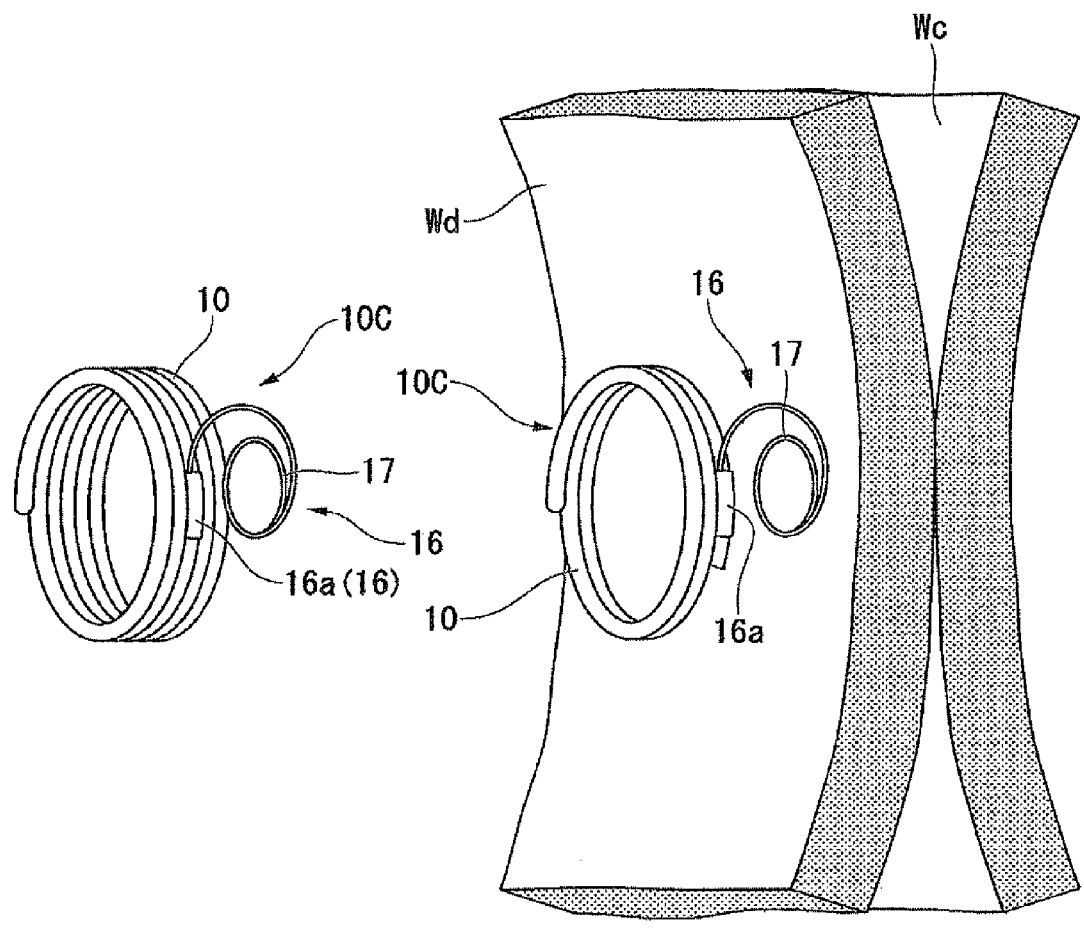

As shown in FIG. 16, a tissue fastening tool 10C is further provided with a wire 17 wound into a coil shape separately from the wire 10. One end of the wire 17 is inserted into the tubular member 16a and is fixed to the wire 10 with adhesive filled into the tubular member 16a so that the wire 17 is branched away from the wire 10. The wire 17 contacts the wall Wd of the duodenum Dd with a tubular member 16a, and thereby it is prevented the tissue fastening tools 10C being pulled into the common bile duct Cb.

Figure 17:
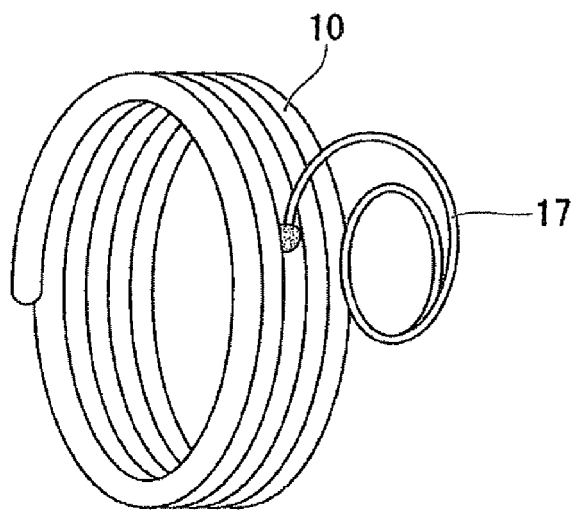

Alternatively, a tubular member 16a may be formed of plastic deformable materials such as metals so that the wire 17 is fixed to the wire 10 by caulking the tubular member 16a. Furthermore, as shown in FIG. 17, one end of the wire 17 may be directly fixed to the wire 10 by welding without accompanying the tubular member 16a.

Figure 18:
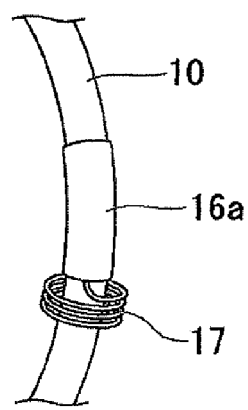
Figure 19:
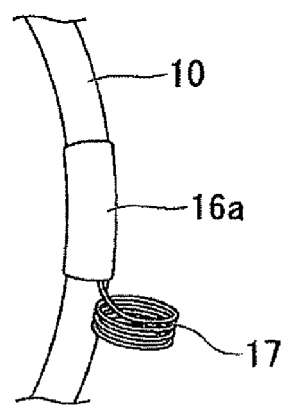

As shown in FIG. 18, after inserting the wire 10 into the inside of the wound wire 17, one end of the wire 17 may be fixed to the main body of the tissue fastening tools 10C. In addition, as shown in FIG. 19, after disposing the wire 17 adjacent to the wire 10, one end of the wire 17 may be fixed to the wire 10.

Figure 20:
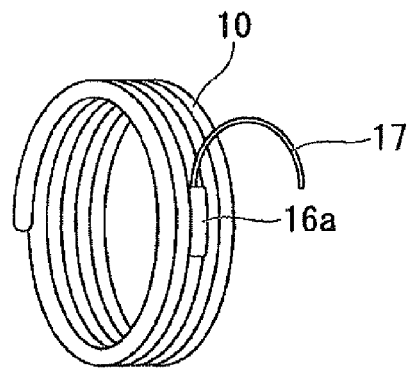

The wire 17 may not have to be wound into the coil shape. For example, as shown in FIG. 20, the wire 17 may be formed in a hook shape.

Figure 21:
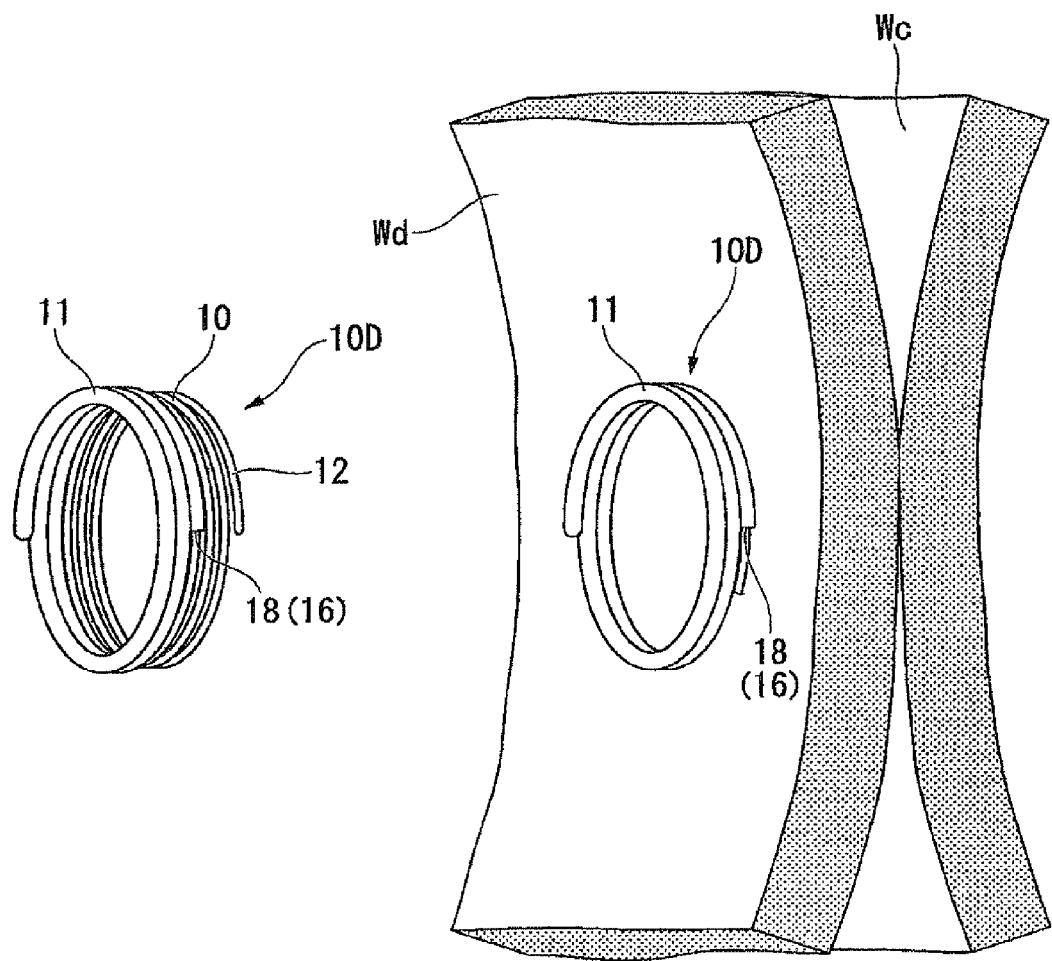

In a tissue fastening tool 10D shown in FIG. 21, an outer diameter of the first tissue fixing section 11 is larger than that of the second tissue fixing section 12. Therefore, a bump 18 having the same effect as the anchor 16 is formed between the first tissue fixing section 11 and the second tissue fixing section 12. The bump 18 contacts the wall Wd of the duodenum Dd, and thereby it is prevented the tissue fastening tools 10D being pulled into the common bile duct Cb.

Figure 22:
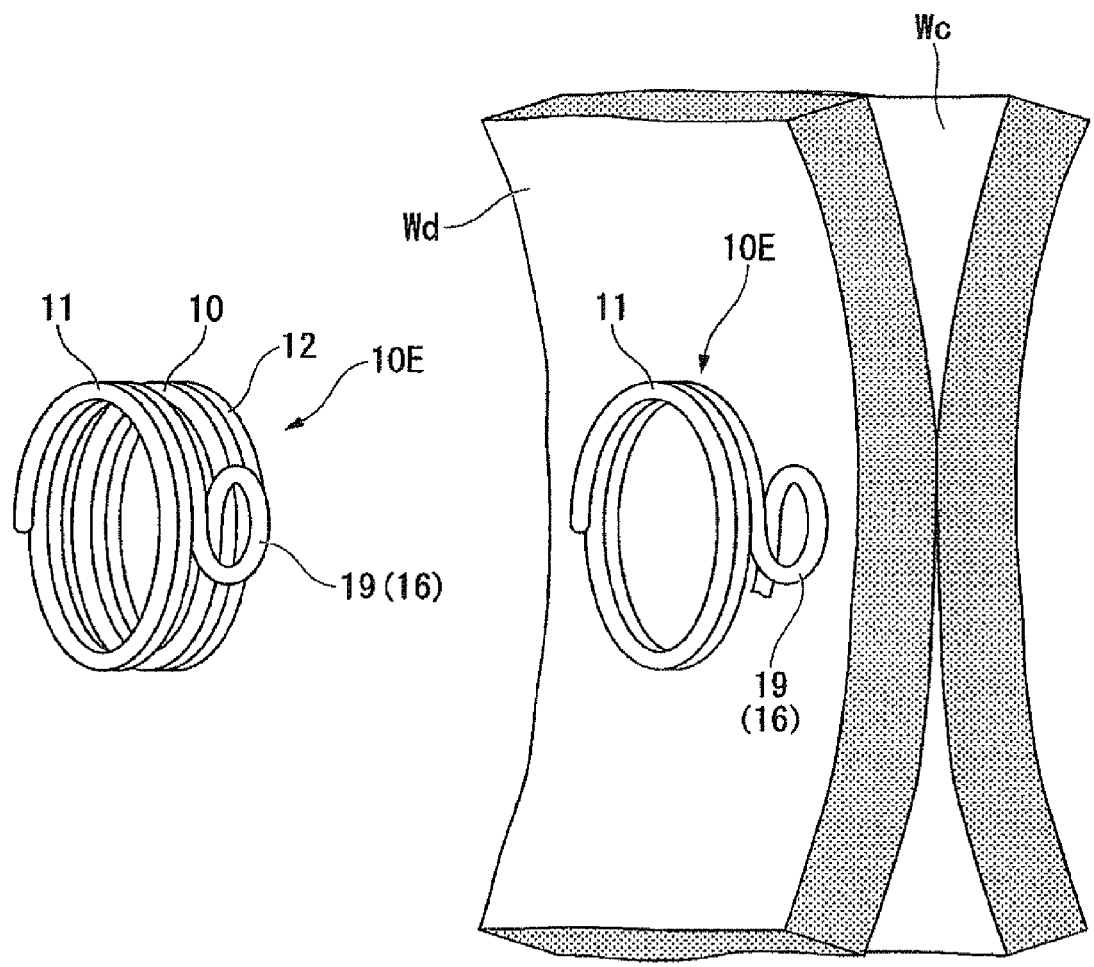

In a tissue fastening tool 10E shown in FIG. 22, a part of the wire 10 located between the first tissue fixing section 11 and the second tissue fixing section 12 forms into a coil shape wound by one reel to an opposite direction to that of the first tissue fixing section 11 and the second tissue fixing section 12. Therefore, a coil portion 19 having the same effect as the anchor 16 is formed between the first tissue fixing section 11 and the second tissue fixing section 12. The coil portion 19 contacts the wall Wd of the duodenum Dd, and thereby it is prevented the tissue fastening tools 10E being pulled into the common bile duct Cb.

Figure 23:
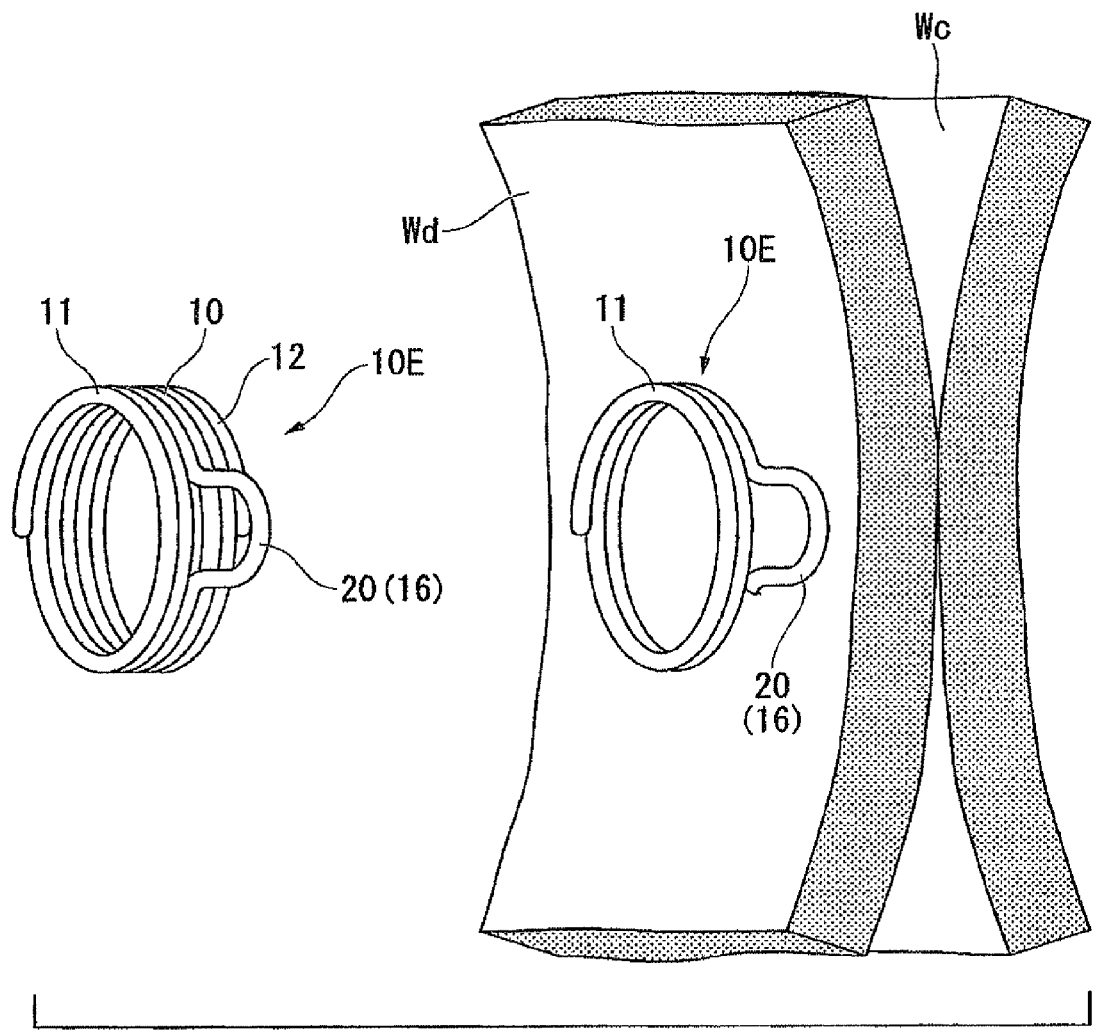

Alternatively, as shown in FIG. 23, a projected section protruded from the first tissue fixing section 11 and the second tissue fixing section 12 may be formed by bending the part of the wire located between the first tissue fixing section 11 and the second tissue fixing section 12 in an opposite winding direction from the first tissue fixing section 11 and the second tissue fixing section 12. Therefore, a projection 20 having the same effect as the anchor 16 is formed between the first tissue fixing section 11 and the second tissue fixing section 12.

Figure 24:
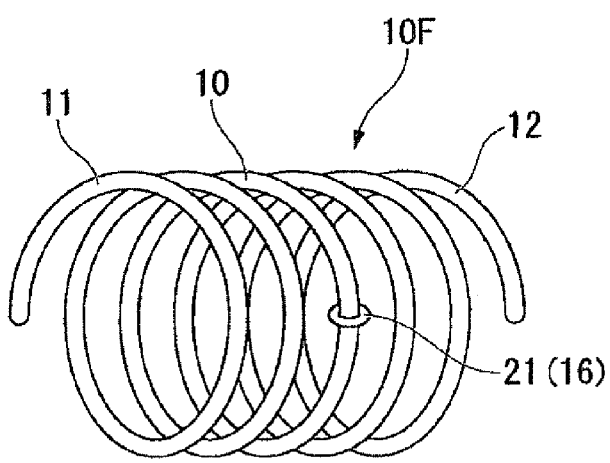

As shown in FIG. 24, a tissue fastening tool 10F is further provided with a ring member 21 having the same effect as the anchor 16 between the first tissue fixing section 11 and the second tissue fixing section 12, separately from the wire 10. The ring member 21 is formed of elastic materials such as elasticized rubber. The wire 10 is passed through the ring member 21 and is fixed to the wire 10 by friction exerted therebetween. The ring member 21 contacts the wall Wd of the duodenum Dd, and thereby it is prevented the tissue fastening tools 10F being pulled into the common bile duct Cb.

Figure 25:
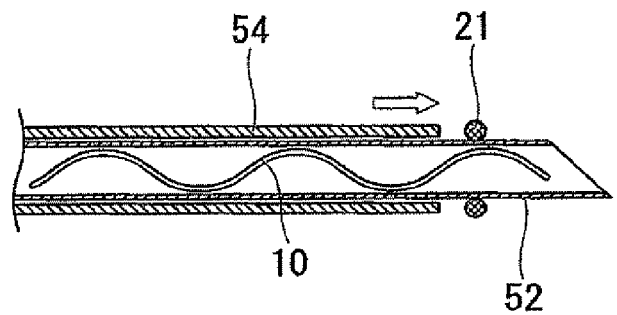
FIG. 25 and FIG. 26 show steps in which the tissue fastening tool shown in FIG. 24 is being dispensed.
Figure 26:
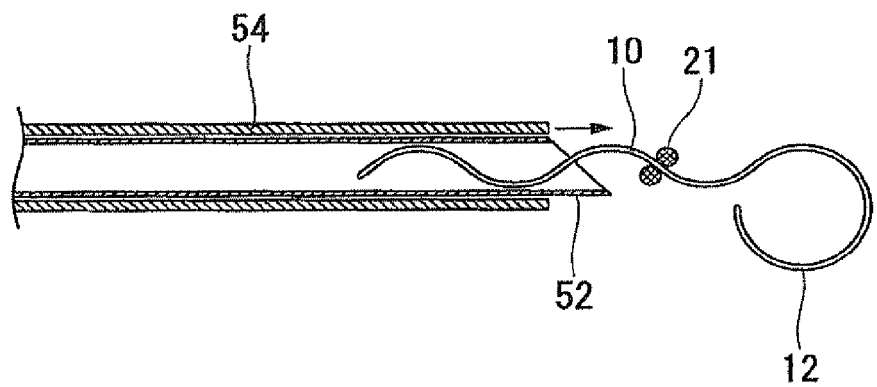

The ring member 21 is not originally disposed at the wire 10. As shown in FIG. 25, the ring member 21 is disposed at the outside of the distal end of the puncturing tool 52 by fastening the distal end of the puncturing tool 52 with its elastic force. The second tissue fixing section 12 is pushed out from the distal end of the puncturing tool 52 penetrating through the wall Wd of the duodenum Dd and the wall Wc of the common bile duct Cb, and then the distal end of the puncturing tool 52 is pulled out from the wall Wd of the duodenum Dd and the wall Wc of the common bile duct Cb. Next, as shown in FIG. 26, the ring member 21 attached to the distal end of the puncturing tool 52 is pushed forward the puncturing tool 52 by advancing the sheath 54 relative to the puncturing tool 52. Therefore, the ring member 21 is fitted to the wire 10 by compression.

Next, a behavior of the stent 30A which is indwelled between the wall Wd of the duodenum Dd and the wall Wc of the common bile duct Cb fastened by the tissue fastening tool 10A will be explained.

When the first ring member 58a and the second ring member 59a are advanced toward the distal end of the applicator main body 51, the stent 30A is pushed by the puncturing section 52 and the distal end of the dilating portion 31 is pressed against the wall Wd of the duodenum Dd and the wall Wc of the common bile duct Cb. The dilating portion 31 is in a conical shape with the diameter expanding from the front end toward the rear end. Therefore, the dilating portion 31 pressed onto the walls Td and Wc advances into a preformed perforation by the puncturing tool 52 so as to expand the perforation, and then penetrates through the walls Wd and We. Once the penetration of the dilating portion 31 through the walls Wd and We is completed, the indwelled portion 32 is indwelled between the walls Wd and Wc. The stent 30A is prevented from falling off from the common bile duct Cb into the duodenum Dd by the dilation of the dilating portion 31. In addition, the stent 30A is prevented from falling off from the duodenum Dd into the common bile duct Cb is prevented by the fall-off prevention portion 33.

Figure 27:
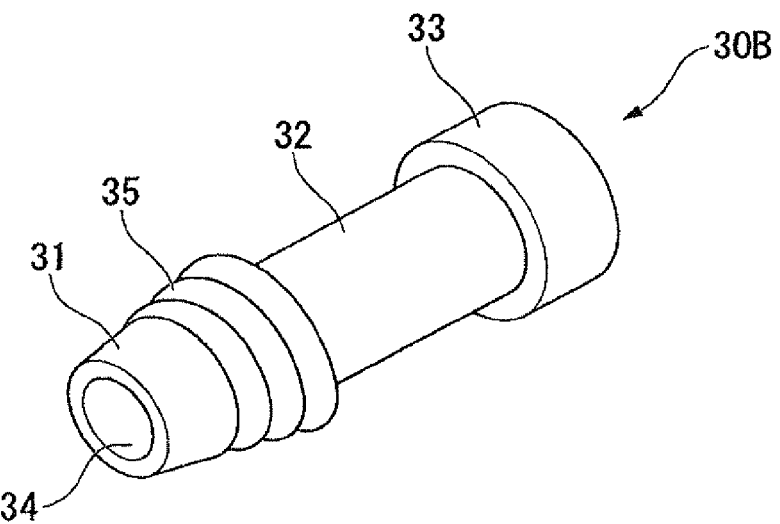
FIG. 27 through FIG. 41 are external views showing modification examples of stents.

The shape of the stent is not limited to the above-described shapes. For example, as shown in FIG. 27, a stent 30B is provided with a spiral screw portion 35 at a part of the circumference of the dilating portion 31 of which the diameter is smoothly expanded from the front end of the stent 30B toward the rear end thereof.

In order to indwell the stent 30B provided with the screw portion 35 at the dilating portion 31 into the wall Wd of the duodenum Dd and the wall Wc of the common bile duct Cb, after a screw 82 is loosened, the applicator main body 51 is rotated around the threaded direction of the screw portion 35 relative to the connector 80 fixed to the endoscope 2 along with moving the first ring member 58a and the second ring member 59a toward the distal end of the applicator main body 51. When the applicator main body 51 is rotated, the stent 30B also rotates in conjunction with the applicator main body 51, and the dilating portion 31 advances easily into the walls Wd and Wc depending on the shape of the screw portion 35. After the dilating portion 31 penetrates the walls Wd and We, the screw portion 35 prevents the stent 30B from falling off from the walls Wd and Wc reliably.

Figure 28:
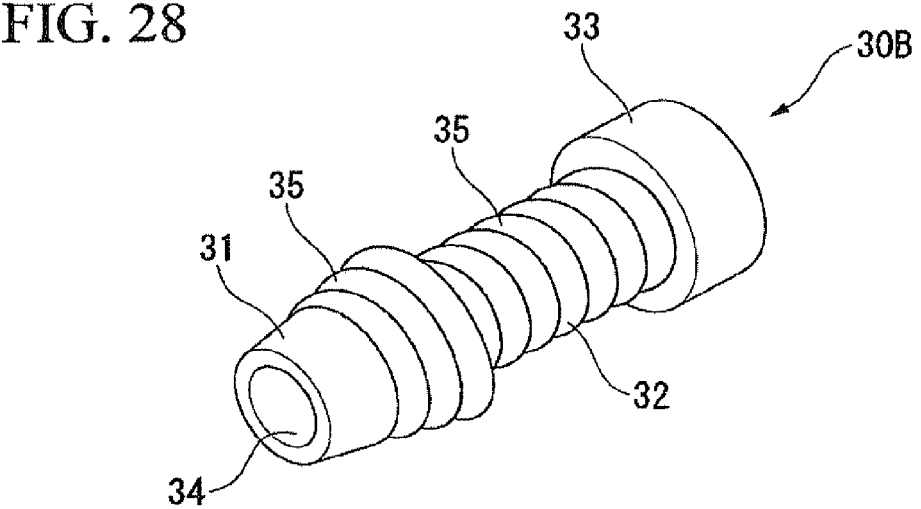
Figure 29:
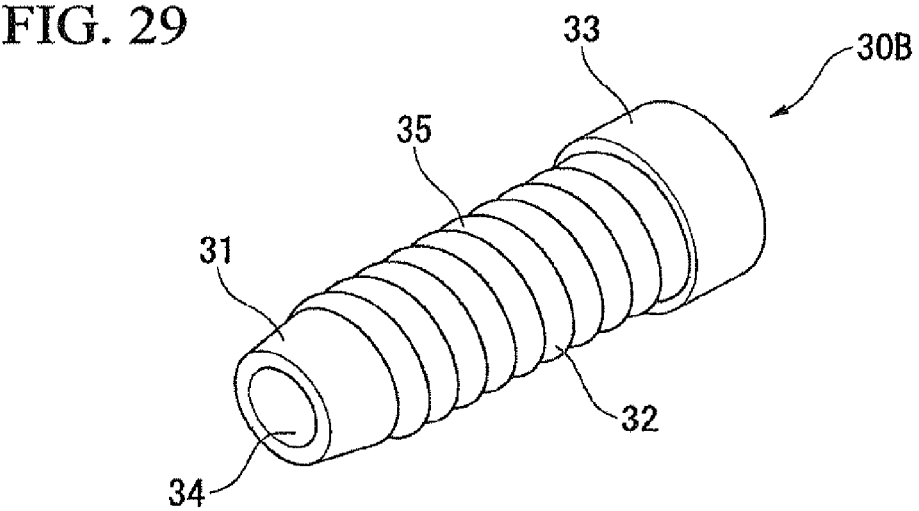

Alternatively, as shown in FIG. 28, the screw portion 35 may be formed so as to be continuous with the indwelled portion 32. Also, as shown in FIG. 29, the screw portion 35 may be formed so that the diameter thereof is uniform from the dilating portion 31 to the indwelled portion 32. The screw portion 35 which is formed on the indwelled portion 32 as well as the dilating portion 31 prevents the stent 30B from falling off from the walls Wd and Wc reliably.

Furthermore, the uneven protrusions formed on the dilating portion 31 and/or the indwelled portion 32 may not be limited to the screw 35. For example, the uneven protrusions may be uniformly formed in a bellows shape. Also, an irregular shape may be employed as seen in a cutting portion 37 which will be described below.

Figure 30:
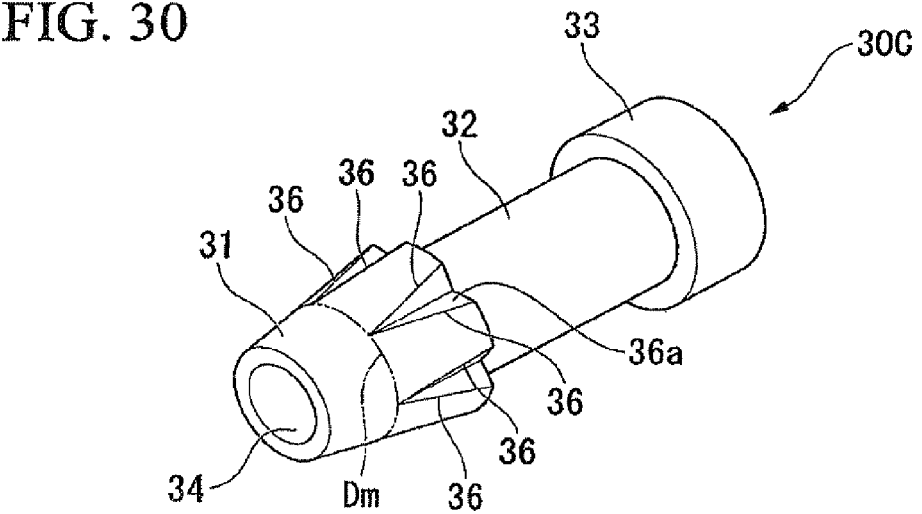

As shown in FIG. 30, a stent 30C is provided with a plurality of ridges 36 formed on the circumference of the dilating portion 31 of which the diameter smoothly expands from the front end of the stent 30C toward the rear end. Each of the ridges 36 is formed sharply and extends from the middle of the dilating portion 31 toward the rear end. A plurality of grooves 36a are formed on the dilating portion 31 along the longitudinal direction of the stent 30C. The ridges 36 are formed at intersections of the inner surface of the groove 36a and the outer periphery surface of the dilating portion 31.

When the first ring member 58a and the second ring member 59a are moved toward the distal end of the applicator main body 51, the stent 30C is pushed along the puncturing tool 52 and the distal end of the dilating portion 31 is pressed against the wall Wd of the duodenum Dd and the wall Wc of the common bile duct Cb. The dilating portion 31 advances while tearing biological tissues of the walls Wd and Wc by the sharp ridges, and then penetrates through the walls Wd and We. Therefore, the penetration of the dilating portion 31 to the wall Wd of the duodenum Dd and the wall Wc of the common bile duct Cb is more easily performed.

A front end of the ridge 36 is located on the dilating portion 31 where the outer diameter of the dilating portion 31 is substantially 2 mm and the ridge 36 is formed rearward this section. If the front end of the ridge 36 is located where the outer diameter of the dilating portion 31 is substantially greater than 2 mm (shown as Dm in FIG. 30), a greater force is required to push a section in which the ridge 36 is not formed into the biological tissues. As a result, the penetration of the dilating portion 31 into the wall Wd of the Duodenum Dd and the wall Wc of the Common bile duct Cb will be difficult.

Figure 31:
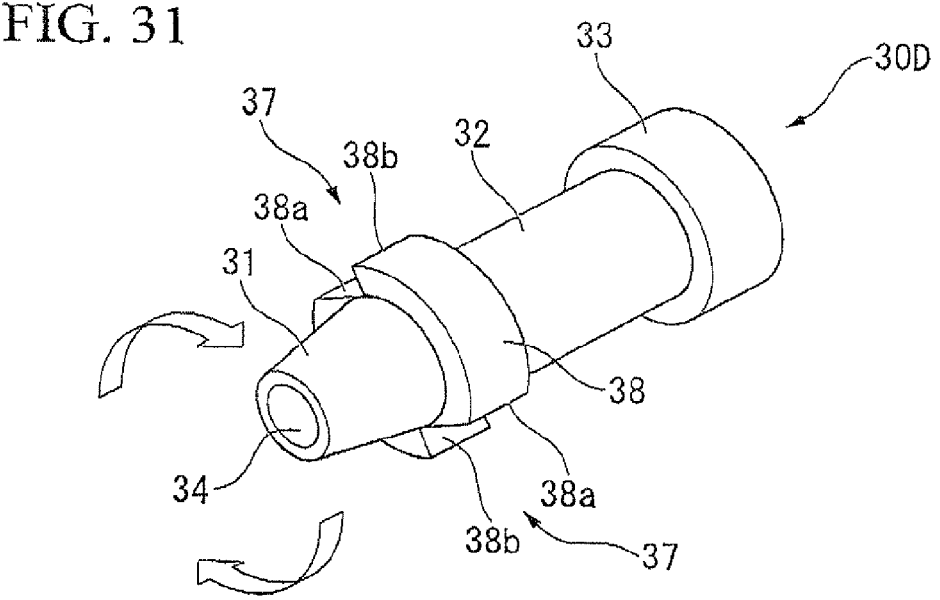

As shown in FIG. 31, a stent 30D is provided with the cutting portions 37 formed on the circumference of the dilating portion 31 of which the diameter smoothly expands from the front end of the stent 30C toward the rear end. Each of the cutting portions 37 extends from the middle of the dilating portion 31 toward the rear end. The cutting portion 37 is provided with a large-diameter portion 38 on the middle of the dilating portion 31 toward the indwelled portion 32, and open-cut portion 38a is formed in the large-diameter portion 38 along the longitudinal direction of the stent 30D. Ridge 38b is formed in an intersection of the open-cut portion 38a and a periphery surface of the large-diameter portion 38.

The applicator main body 51 is rotated around the cutting direction of the cutting portion 37 relative to the connector 80 fixed to the endoscope 2 along with moving the first ring member 58a and the second ring member 59a toward the distal end of the applicator main body 51. Thereby, the stent 30D also rotates in conjunction with the applicator main body 51 in a direction shown by an arrow in the figure, and the dilating portion 31 advances while tearing biological tissues of the walls Wd and Wc by the sharp ridges 38b of the cutting portions 37, and then penetrates through the walls Wd and Wc. Therefore, the penetration of the dilating portion 31 to the wall Wd of the duodenum Dd and the wall Wc of the common bile duct Cb is more easily performed.

Figure 32:
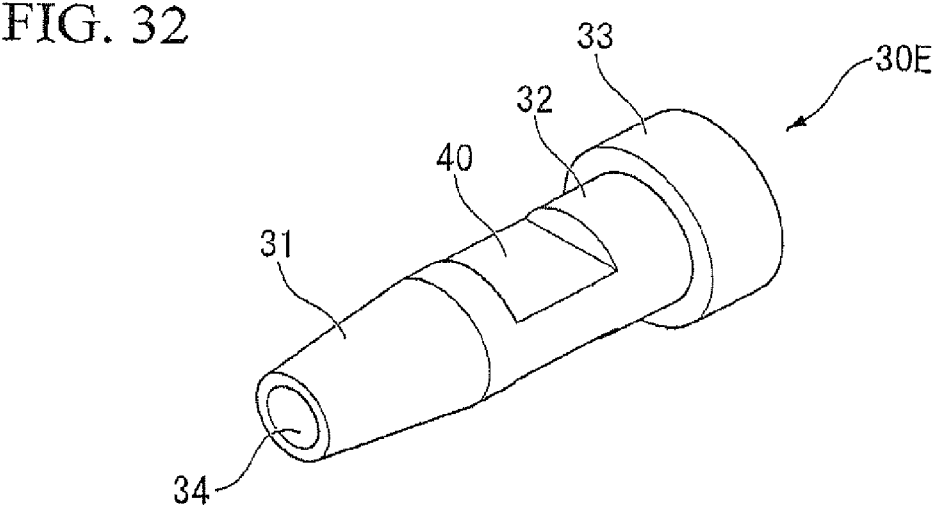

In a stent 30E shown in FIG. 32, a narrowed area 40 is formed in the indwelled portion 32. The narrow portion 40 prevents the stent 30E from falling off from the walls Wd and Wc reliably.

Figure 33:
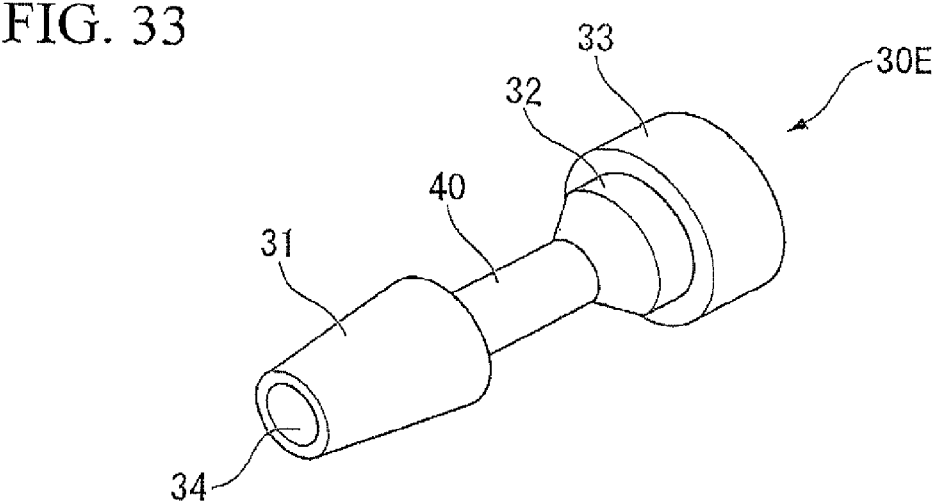

Alternatively, the narrowed area 40 may not be limited to a constricted portion shown in the FIG. 32. For example, as shown in FIG. 33, the diameter of a part of the indwelled portion 32 may be reduced.

Figure 34:
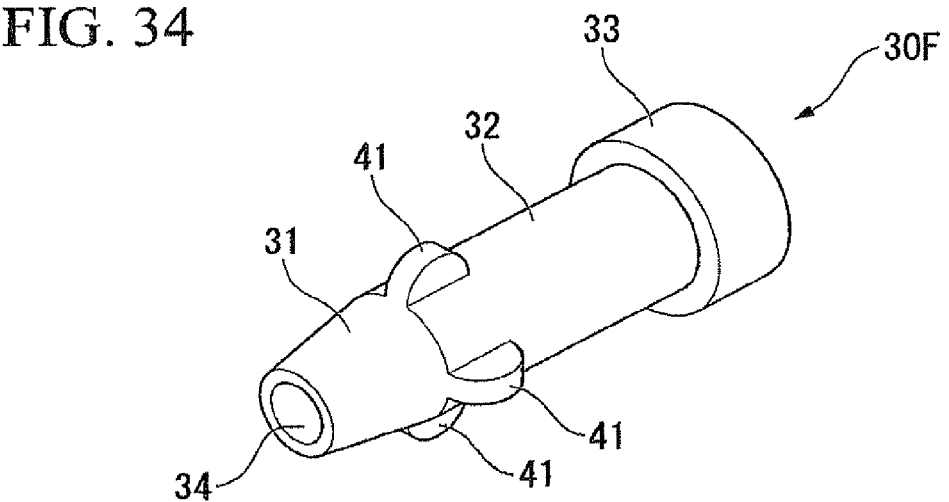

In a stent 30F shown in FIG. 34, projections 41 are formed separately at an equal distance apart on the outer periphery of the dilating portion 31. The projections 41 prevent the stent 30F from falling off from the walls Wd and Wc reliably.

Figure 35:
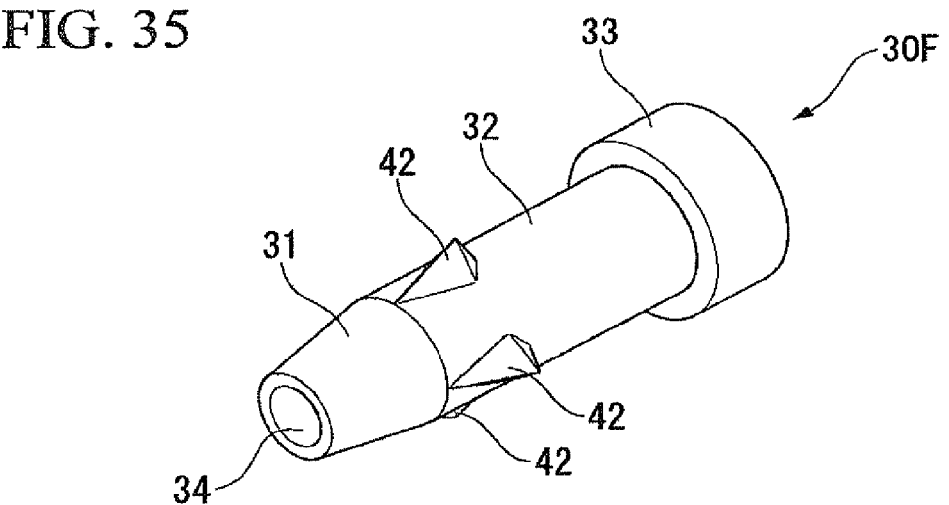
Figure 36:
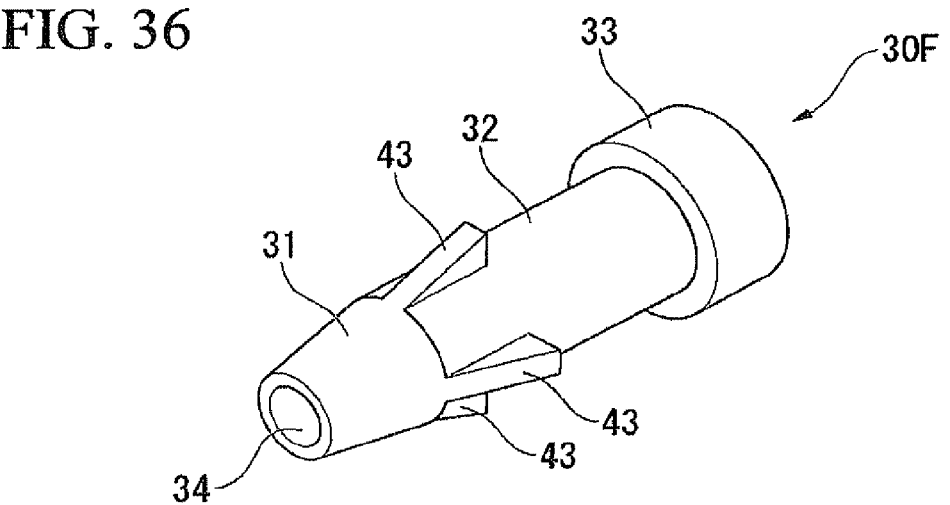

The shapes and number of the projections 41 may not be limited thereto. For example, various shapes of projections 42 and 43 such as shown in FIGS. 35 and 36, respectively may be disposed on the outer periphery of the dilating portion 31.

Figure 37:
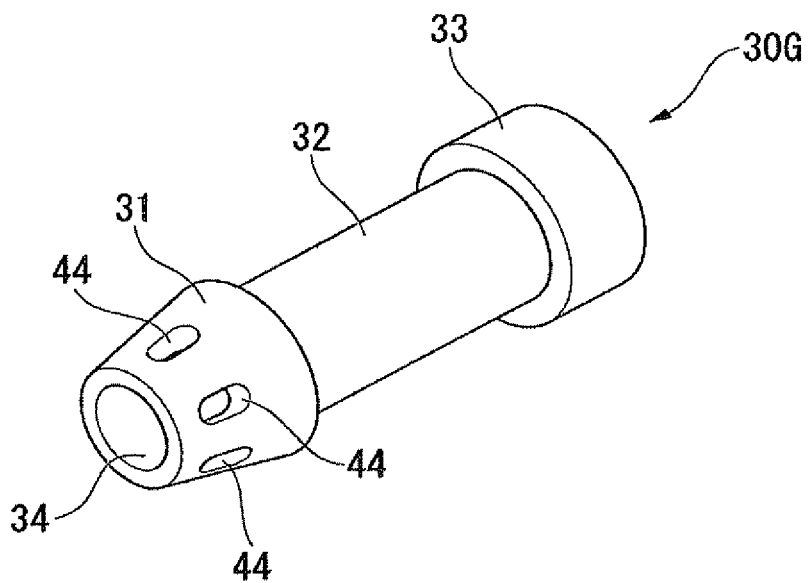

In a stent 30G shown in FIG. 37, small holes 44 which communicate with the through hole 34 are formed on the outer periphery of the dilating portion 31. When the stent 30G is indwelled between the wall Wd of the duodenum Dd and the wall Wc of the common bile duct Cb, the bile flows not only from one end of the through hole 34 on the common bile duct Cb side, but also flows into the through hole 34 through the small holes 44. Therefore, the flow of bile via the stent 30G can be improved.

Figure 38:
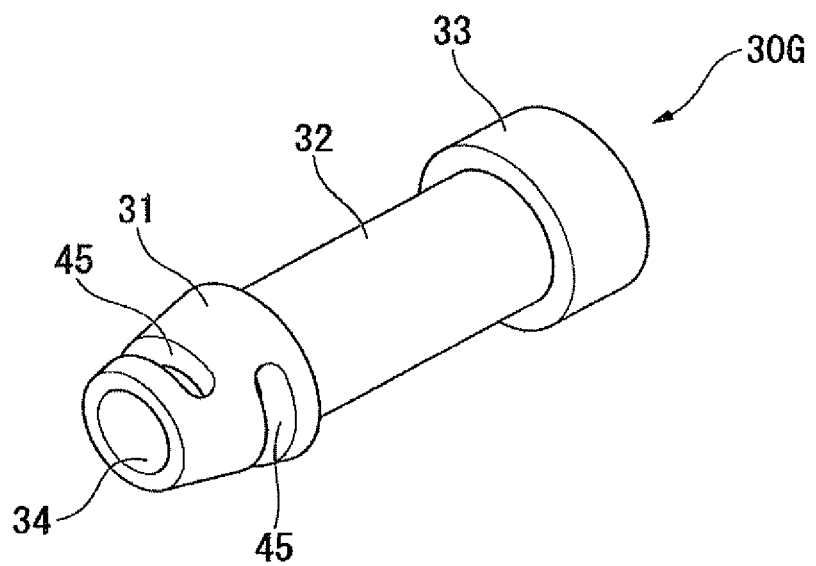

Note that the shapes and number of the small holes 44 may not be limited thereto. For example, small holes 45 shown in FIG. 38 may be formed in the dilating portion 31.

Figure 39:
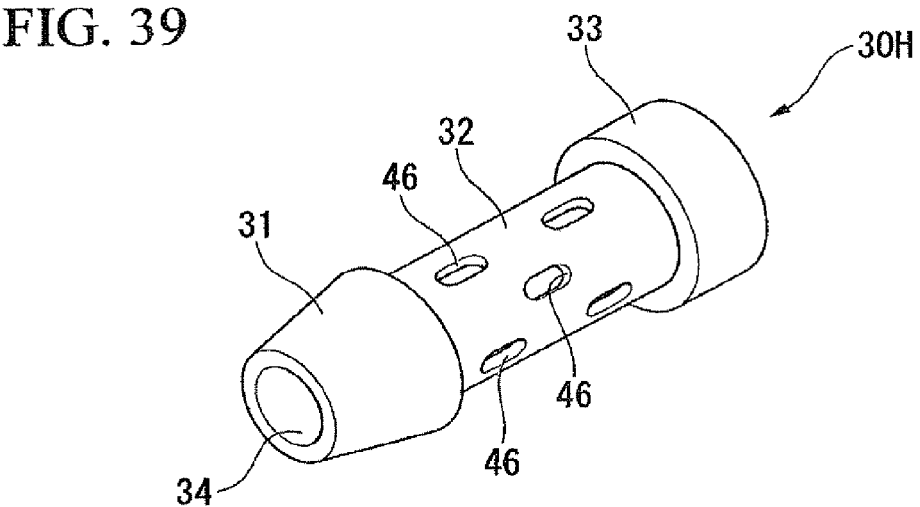

In a stent 30H shown in FIG. 39, small holes 46 which communicate with the through hole 34 formed on the outer periphery of the indwelled portion 32. When the stent 30G is indwelled between the wall Wd of the duodenum Dd and the wall Wc of the common bile duct Cb, the bile flowing through the through hole 34 will come into contact with an area of the walls Wd and Wc fastened by the tissue fastening tool 10A, via the small holes 46. The walls Wd and Wc fastened by the tissue fastening tool 10A coalesce around the entire circumference of the tissue fastening tool 10A, and a fistula is formed. An inflammation occurs upon contacting with the bile in the process of recovery, which promotes the coalescence of the walls Wd and Wc.

Figure 40:
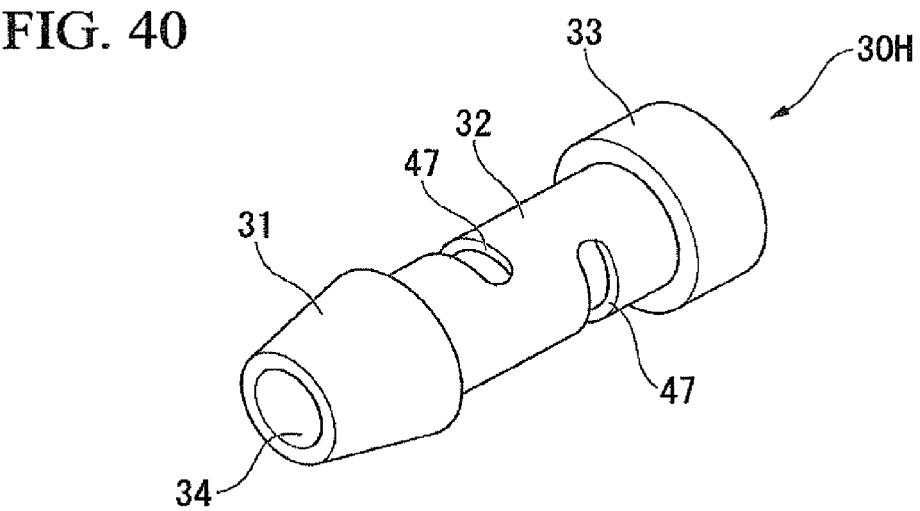
Figure 41:
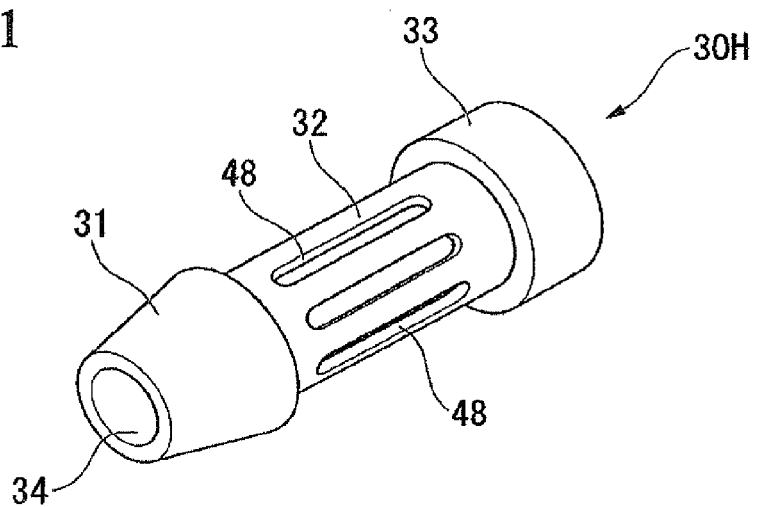

Note that the shapes and number of the small holes 46 may not be limited thereto. For example, small holes 47, 48 such as shown in FIGS. 40 and 41, respectively may be formed on the outer periphery of the indwelled portion 32. Furthermore, small holes shown in FIGS. 37 to 41 may be combined with the stents shown in FIGS. 27 to 36.

Figure 42:
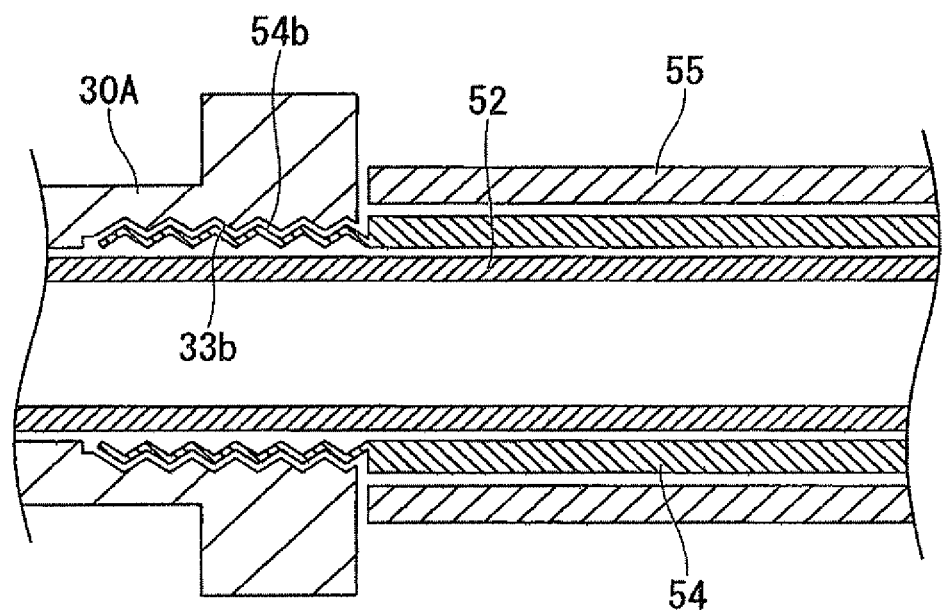
FIG. 42 is a cross-sectional view showing a modification example of the fixed section of the sheath and the stent.

According to the present embodiment, the small holes 54a are formed at the distal end of the sheath 54 and the projections 33a which can be engaged to the small holes 54a are formed in the stent 30A. Alternatively, as shown in FIG. 42, a bellows portion 54b may be disposed at the distal end of the sheath 54 and bellows-shaped projections 33b may be disposed on the inner peripheral surface of the stent 30A (including the stents 30B to 300H). The projections 33b are fitted to the bellows portion 54b so that the both of them engage each other, and thereby the stent 30A can be detachably disposed at the distal end of the sheath 45.

Figure 43:
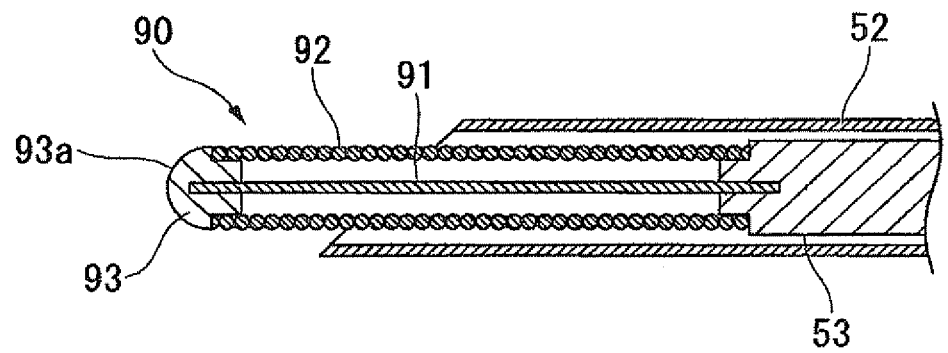
FIG. 43 is an external view showing a modification example of the applicator.

The structure of the applicator may not be limited to the above described features. For example, in an applicator shown in FIG. 43, a flexible portion 90 which is softer than other parts of the stylet 53 is disposed at the distal end of the stylet 53. That is, a cored bar 91 which is thinner than the stylet 53 is connected to the distal end of the stylet 53, such that the cored bar 91 protrudes forward. A flexible coil 92 made of metals or synthetic resins is disposed around the cored bar 91 so that the cored bar 91 is inserted into the coils 92. An outer diameter of the coil 92 is substantially equal to that of the stylet 53, and an outer periphery of the coil 92 is smoothly connected to the outer periphery of the stylet 53. A sealing chip 93 is fixed to the distal end of the cored bar 91 so as to seal the distal end of the coil 92. The distal surface 93a of the sealing chip 93 is formed in a smooth manner.

For example, when the stent 30A is indwelled between the walls Wd and Wc, the flexible portion 90 of the stylet 53 is made to protrude from the sharp distal end of the puncturing tool 52. Therefore, even if the flexible portion 90 comes into contact with surrounding body tissues, since the flexible portion 90 is deformed by defecting the cored bar 91 and the coils 92, damage to the tissues by the sharp distal end of the puncturing tool 52 is reliably prevented.

Second Embodiment

The second embodiment of the present invention will be explained. In the following description, components that are the same as the first embodiment shall be provided with the same numeric symbol and redundant descriptions shall be omitted.

Figure 44:
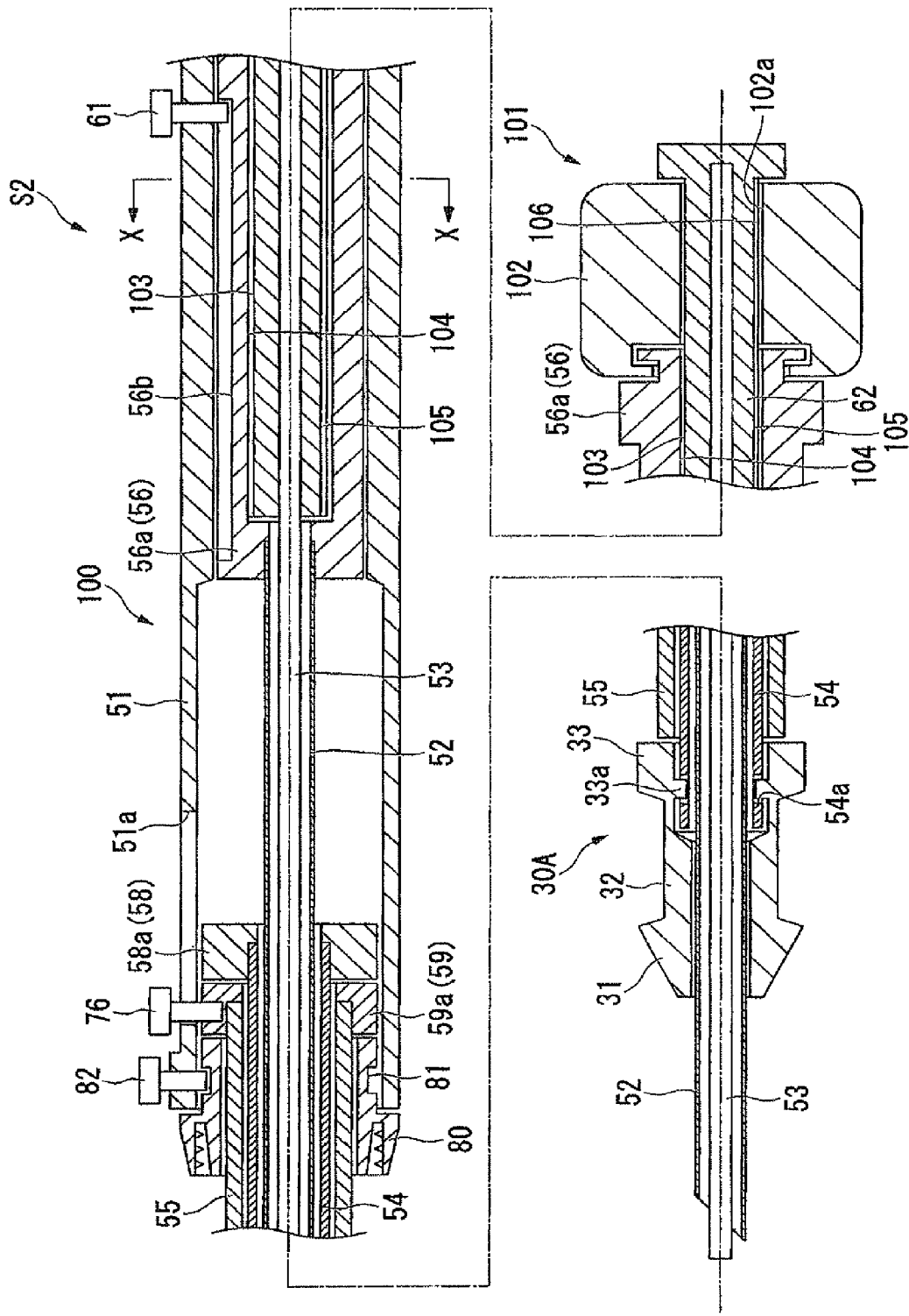
FIG. 44 shows a tissue fastening apparatus in the second embodiment of the present invention and is a cross-sectional view showing the internal structures of a tissue fastening tool, a stent and an applicator included in the apparatus.

As shown in FIG. 44, a tissue fastening apparatus S2 of the present embodiment includes the tissue fastening tool 10A, the stent 30A and an applicator 100. A stylet operation portion 101 of the applicator 100 includes the tubular second shaft 62 which is inserted from the rear end of the first shaft 56a thereinto and a grip 102 is provided at the rear end of the first shaft 56a which supports the puncturing tool 52 so as to be rotatably supported around the axis along the longitudinal direction of the first shaft 56a. A through hole 102a which passes through the longitudinal direction of the first shaft 56a is formed in the grip 102. The second shaft 62 is inserted into the through hole 102a.

Figure 45:
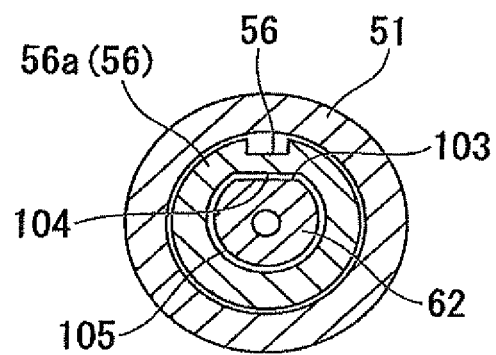
FIG. 45 is a cross-sectional view of the applicator as seen from the line X-X in FIG. 42.

As shown in FIG. 45, a flat surface 103 which is parallel to the axis along the longitudinal direction of the second shaft 62 is formed on the outer periphery surface of the second shaft 62 from the front end of the second shaft 62 to the rear end. Therefore, a cross-sectional shape of the second shaft 62 which is orthogonal to the longitudinal direction of the second shaft 62 forms a substantially circular shape with a flat section. On the other hand, at an inner peripheral surface of the first shaft 56*a* into which the second shaft 62 is inserted, a flat surface 104 which is parallel to the axis of the longitudinal direction of the first shaft 56*a* is formed. Therefore, a cross-sectional shape of an inner space of the first shaft 56*a* forms a substantially circular shape with a flat section, same as the shape of the second shaft 62. When the second shaft 62 is inserted into the first shaft 56*a* with the flat surface 103 and the flat surface 104 are facing each other, the rotation of the second shaft 62 around the axis of the longitudinal direction of the second shaft 62 relative to the first shaft 56*a* is restricted.

In addition, a thread ridge 105 is formed on the outer peripheral surface of the second shaft 62 from the front end of the second shaft 62 to the rear end. On the other hand, a thread groove 106 which engages with the thread ridge 105 is formed on an inner surface of the through hole 102*a* of the grip 102. When the grip 102 is rotated in one direction, the second shaft 62 of which the thread ridge 105 is engaged with the thread groove 106 of the grip 102 is pushed into the first shaft 56*a*. When the grip 102 is rotated in the other direction, the second shaft 62 is pulled out from the first shaft 56*a*.

An insertion length of the second shaft 62 into the first shaft 56*a* per rotation of the grip 102 is uniform. Therefore, it is possible to control the insertion length of the second shaft 62 into the first shaft 56*a* as per number of rotations of the grip 102. That is, the insertion length of the stylet 53 into the puncturing tool 52 as per number of rotations of the grip 102 can be controlled. This mechanism indicates that the length of the tissue fastening tool 10A dispensed from the distal end of the puncturing tool 52 can be controlled as per number of rotations of the grip 102.

When the tissue fastening tool 10A forms into a coil shape as described in this embodiment, the insertion length of the stylet 53 per rotation of the grip 102 is preferred to be substantially n or 1/n times (n is a positive integer) the circumference of the tissue fastening tool 10A. For example, if the insertion length of the stylet 53 per rotation of the grip 102 is substantially equal to the circumference of the tissue fastening tool 10A, the tissue fastening tool 10A is dispensed from the distal end of the puncturing tool 52 by one reel length every time the grip 102 is rotated once. Furthermore, if the second tissue fixing section 12 consists of two reel lengths of the tissue fastening tool 10A, only the second tissue fixing section 12 can be dispensed from the distal end of the puncturing tool 52 by rotating the grip 102 twice. Alternatively, if an insertion length of the stylet 53 per rotation of the grip 102 is substantially equal to a half of the circumference of the tissue fastening tool 10A, the tissue fastening tool 10A is dispensed from the distal end of the puncturing tool 52 by a half reel length every time when the grip 102 is rotated once. Furthermore, if the second tissue fixing section 12 consists of two reel lengths of the tissue fastening tool 10A, only the second tissue fixing section 12 can be dispensed from the distal end of the puncturing tool 52 by rotating the grip 102 four times.

When the procedure to make a bypass between the common bile duct and the duodenum after joining them using the tissue fastening apparatus S2 as described above is performed similar to the first embodiment. The sharp distal end of the puncturing tool 52 is pierced into the wall Wd of the duodenum Dd and the wall Wc of the common bile duct Cb, and then the second shaft 62 is pushed into the first shaft 56*a* by a predetermined length by rotating the grip 102 in one direction at predetermined times. Therefore, the stylet 53 changes its position relative to the puncturing tool 52 and the second tissue fixing section 12 of the tissue fastening tool 10A are pushed out form the distal end of the puncturing tool 52. When the second tissue fixing section 12 is pushed out from the puncturing tool 52, the second tissue fixing section 12 is restored to its original coil shape and is hooked onto the inside surface of the wall Wc of the common bile duct Cb.

After the distal end of the puncturing tool 52 slightly separates from the inside surface of the wall Wd of the duodenum Dd, the second shaft 62 is pushed into the first shaft 56*a* by a predetermined length by rotating the grip 102 again in one direction at predetermined times. Therefore, the stylet 53 changes its position relative to the puncturing tool 52 and the coupling section 13 and the first tissue fixing section 11 of the tissue fastening tool 10A are pushed out form the distal end of the puncturing tool 52. When the first tissue fixing section 11 is pushed out from the puncturing tool 52, the first tissue fixing section 11 is restored to its original coil shape and is hooked onto the inner side of the wall Wd of the duodenum Dd.

According to the applicator 100, the tissue fastening tool 10A can be pushed out from the puncturing tool 52 easily with high precision by simply rotating the grip 102. In addition, the stent 30A can be separated from the distal end of the sheath 54 in a timely manner. As a result, the tissue fastening tool 10A and the stent 30A can be indwelled at any desired position within the body.

What is claimed is:

1. A tissue fastening tool which fastens a first biological tissue and a second biological tissue adjacent to the first biological tissue, comprising:
    an elastic wire which has a predetermined length to be indwelled to the first biological tissue and second biological tissue by piercing, and which is configured to be restored to a predetermined coiled shape, wherein
    the wire includes:
    a first wire and a second wire;
    a first tissue fixing section which is disposed on a first end of the first wire and which is configured to be hooked onto the first biological tissue;
    a second tissue fixing section which is disposed on a second end of the first wire and which is configured to be hooked onto the second biological tissue; and
    an anchor which is formed of the second wire different from the first wire and which is secured to the first wire between the first tissue fixing section and the second tissue fixing section, a first end of the anchor is fixed to the first wire and a second end of the anchor is configured to be restored so as to form a loop, and wherein
    the first wire including the first tissue fixing section and the second tissue fixing section is configured to be restored to a predetermined coiled shape wound with a predetermined diameter, and
    when the second wire is restored, the anchor is formed in the loop such that the anchor has a central axis disposed outside of the predetermined diameter of the first tissue fixing section and the second tissue fixing section.

2. The tissue fastening tool according to claim 1, wherein the anchor is formed of a coil shape which is wound into a direction opposite from a winding direction of the first tissue fixing section and the second tissue fixing section.

3. The tissue fastening tool according to claim 1, wherein the anchor is a projection formed by bending the second wire in a winding direction opposite from the first tissue fixing section and the second tissue fixing section.

4. The tissue fastening tool according to claim 1, wherein the central axis of the anchor and a center axis of the predetermined coiled shape of the first wire are set to be parallel to each other.

5. An applicator comprising:
   a tubular puncturing tool housing the tissue fastening tool according to claim 1;
   a fastening tool pusher which is inserted into the puncturing tool and dispenses the tissue fastening tool inserted into the puncturing tool from a distal end of the puncturing tool; and
   a sheath in which the puncturing tool is inserted, the sheath configured to shift a stent attached at the distal end of the sheath relative to the puncturing tool.

6. The applicator according to claim 5, further comprising:
   a fastening tool pusher operating section which shifts the fastening tool pusher relative to the puncturing tool.

7. The applicator according to claim 6, wherein
   the fastening tool pusher operating section comprises:
   a lever swingably disposed on a member which supports the puncturing tool; and
   a linkage which translates an swinging motion of the lever into a linear motion of the fastening tool pusher along the puncturing tool.

8. The applicator according to claim 7, wherein a moving distance of the fastening tool pusher per operation on the lever is substantially n or 1/n times (n is a positive integer) the circumference of the tissue fastening tool when the tissue fastening tool forms into a coil shape.

9. The applicator according to claim 6, wherein
   the puncturing tool pusher operating section comprises:
   a grip rotatably disposed at the applicator main body; and
   a linkage which translates rotation motion of the grip into a liner motion of the tissue fastening tool along the puncturing tool.

10. The applicator according to claim 9, wherein a moving distance of the fastening tool pusher per 360-degree roll of the grip is substantially n or 1/n times (n is a positive integer) the circumference of the tissue fastening tool when the tissue fastening tool forms into a coil shape.

11. The applicator according to claim 5, wherein a mounting section which allows the stent detachably attach to a distal end of the sheath is disposed at the distal end of the sheath.

12. The applicator according to claim 5, further comprising:
    a stent pusher for separating the stent attached to a distal end of the sheath from the sheath.

13. The applicator according to claim 5, wherein a distal end surface of the fastening tool pusher is formed in a smooth manner.

14. The applicator according to claim 13, wherein a front portion of the fastening tool pusher including the distal end surface is formed in a flexible manner.

15. A tissue fastening apparatus comprising:
    the tissue fastening tool according to claim 1;
    a stent provided with a dilating portion having a diameter which increases from a front end to a rear end of the dilating portion, an indwelled portion which is connected the dilating portion, and a through hole which passes through the dilating portion and the indwelled portion in a longitudinal direction of the stent; and
    an applicator provided with a tubular puncturing tool in which the tissue fastening tool is inserted, a fastening tool pusher inserted into the puncturing tool to dispense the tissue fastening tool inserted into the puncturing tool from a distal end of the puncturing tool, and a sheath into which the puncturing tool is inserted, the sheath configured to shift the stent which is detachably disposed at the distal end of the sheath relative to the puncturing tool.

* * * * *